US012672915B2

(12) United States Patent
Cook et al.

(10) Patent No.: US 12,672,915 B2
(45) Date of Patent: Jul. 7, 2026

(54) CONNECTOR FOR MULTIPLEXER OPTICAL COUPLING

(71) Applicant: Boston Scientific Scimed, Inc., Maple Grove, MN (US)

(72) Inventors: Christopher A. Cook, Laguna Niguel, CA (US); Eric Schultheis, San Clemente, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 532 days.

(21) Appl. No.: 17/882,586

(22) Filed: Aug. 7, 2022

(65) Prior Publication Data
US 2023/0064371 A1      Mar. 2, 2023

Related U.S. Application Data

(60) Provisional application No. 63/236,633, filed on Aug. 24, 2021.

(51) Int. Cl.
*A61B 18/20*        (2006.01)
*A61B 18/24*        (2006.01)
(Continued)

(52) U.S. Cl.
CPC .. *A61B 18/245* (2013.01); *A61B 2018/00285* (2013.01); *A61B 2018/00369* (2013.01); *A61B 2018/2211* (2013.01)

(58) Field of Classification Search
CPC ............................ A61B 18/22–26; G02B 6/38
See application file for complete search history.

(56) References Cited

U.S. PATENT DOCUMENTS 4,649,924 A    3/1987   Taccardi
4,699,147 A    10/1987  Chilson et al.
(Continued)

FOREIGN PATENT DOCUMENTS

AU    2017205323    1/2022
AU    2019452180    1/2022
(Continued)

OTHER PUBLICATIONS

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
(Continued)

*Primary Examiner* — Lynsey C Eiseman
(74) *Attorney, Agent, or Firm* — Seager, Tufte & Wickhem, LLP

(57)        ABSTRACT

A catheter system (100) for treating a treatment site (106) within or adjacent to a vessel wall (108A) or a heart valve includes a light source (124), a first light guide (122A), a second light guide (122A), and a guide bundle (152). The light source (124) generates light energy. The first light guide (122A) receives the light energy from the light source (124) and has a guide proximal end (122P). The second light guide (122A) receives the light energy from the light source (124) and has a guide proximal end (122P). A guide bundle (152) is in optical communication with the light source (124). The guide bundle (152) bundles the first light guide (122A) and the second light guide (122A). The guide bundle (152) includes a first ferrule (778) that engages the guide proximal end (122P) of the first light guide (122A) and a second ferrule (778) that engages the guide proximal end (122P) of the second light guide (122A). At least one of the
(Continued)

ferrules (778) can be formed at least partially from a ceramic material or a metallic material.

20 Claims, 7 Drawing Sheets

(51) Int. Cl.
  *A61B 18/00*          (2006.01)
  *A61B 18/22*          (2006.01)

(56)                  References Cited

U.S. PATENT DOCUMENTS

| | | | |
|---|---|---|---|
| 4,799,479 | A | 1/1989 | Spears |
| 4,850,351 | A | 7/1989 | Herman |
| 4,913,142 | A | 4/1990 | Kittrell et al. |
| 4,932,954 | A | 6/1990 | Wondrazek et al. |
| 4,955,895 | A | 9/1990 | Suglyama |
| 4,960,108 | A | 10/1990 | Reichel et al. |
| 4,994,059 | A | 2/1991 | Kosa et al. |
| 4,998,930 | A | 3/1991 | Lundahl |
| 5,019,075 | A | 5/1991 | Spears et al. |
| 5,034,010 | A | 7/1991 | Kittrell et al. |
| 5,041,121 | A | 8/1991 | Wondrazek et al. |
| 5,057,106 | A | 10/1991 | Kasevich et al. |
| 5,082,343 | A | 1/1992 | Coult et al. |
| 5,093,877 | A | 3/1992 | Aita et al. |
| 5,104,391 | A | 4/1992 | Ingle |
| 5,104,392 | A | 4/1992 | Kittrell et al. |
| 5,109,452 | A | 4/1992 | Selvin et al. |
| 5,116,227 | A | 5/1992 | Levy |
| 5,126,165 | A | 6/1992 | Akihama et al. |
| 5,152,768 | A | 10/1992 | Bhatta |
| 5,173,049 | A | 12/1992 | Levy |
| 5,176,674 | A | 1/1993 | Hofmann |
| 5,181,921 | A | 1/1993 | Makita et al. |
| 5,188,632 | A | 2/1993 | Goldenberg |
| 5,200,838 | A | 4/1993 | Nudelman |
| 5,269,777 | A | 12/1993 | Doiron |
| 5,290,277 | A | 3/1994 | Vercimak et al. |
| 5,324,282 | A | 6/1994 | Dodick |
| 5,328,472 | A | 7/1994 | Steinke et al. |
| 5,336,184 | A | 8/1994 | Teirstein |
| 5,363,458 | A | 11/1994 | Pan |
| 5,372,138 | A | 12/1994 | Crowley |
| 5,387,225 | A | 2/1995 | Euteneur |
| 5,400,428 | A | 3/1995 | Grace |
| 5,410,797 | A | 5/1995 | Steinke et al. |
| 5,417,689 | A | 5/1995 | Fine |
| 5,422,926 | A | 6/1995 | Smith |
| 5,431,647 | A | 7/1995 | Purcell |
| 5,454,809 | A | 10/1995 | Janssen |
| 5,456,680 | A | 10/1995 | Taylor |
| 5,474,537 | A | 12/1995 | Solar |
| 5,496,311 | A | 3/1996 | Abele et al. |
| 5,509,917 | A | 4/1996 | Cecchetti |
| 5,519,798 | A * | 5/1996 | Shahid ................. G02B 6/3636 |
| | | | 385/59 |
| 5,540,679 | A | 7/1996 | Fram |
| 5,562,657 | A | 10/1996 | Griffin |
| 5,598,494 | A | 1/1997 | Behrmann et al. |
| 5,609,606 | A | 3/1997 | O'Boyle |
| 5,611,807 | A | 3/1997 | O'Boyle |
| 5,631,985 | A | 5/1997 | Yamada et al. |
| 5,637,877 | A | 6/1997 | Sinofsky |
| 5,661,829 | A | 8/1997 | Zheng |
| 5,697,377 | A | 12/1997 | Wittkamph |
| 5,718,241 | A | 2/1998 | Ben-Haim et al. |
| 5,729,583 | A | 3/1998 | Tang |
| 5,764,843 | A | 6/1998 | Macken et al. |
| 5,772,609 | A | 6/1998 | Nguyen et al. |
| 5,860,974 | A | 1/1999 | Abele |
| 5,891,135 | A | 4/1999 | Jackson et al. |
| 5,906,611 | A | 5/1999 | Dodick et al. |
| 5,944,697 | A | 8/1999 | Benett et al. |

| | | | |
|---|---|---|---|
| 6,007,514 | A | 12/1999 | Nita |
| 6,015,404 | A | 1/2000 | Altshuler |
| 6,080,119 | A | 6/2000 | Schwarze et al. |
| 6,123,923 | A | 9/2000 | Unger |
| 6,139,510 | A | 10/2000 | Palermo |
| 6,186,963 | B1 | 2/2001 | Schwarze et al. |
| 6,203,537 | B1 | 3/2001 | Adrian |
| 6,210,404 | B1 | 4/2001 | Shadduck |
| 6,339,470 | B1 | 1/2002 | Papademetriou et al. |
| 6,356,575 | B1 | 3/2002 | Fukumoto |
| 6,368,318 | B1 | 4/2002 | Visuri et al. |
| 6,423,055 | B1 | 7/2002 | Farr |
| 6,500,174 | B1 | 12/2002 | Maguire et al. |
| 6,514,203 | B2 | 2/2003 | Bukshpan |
| 6,514,249 | B1 | 2/2003 | Maguire |
| 6,524,251 | B2 | 2/2003 | Rabiner et al. |
| 6,538,739 | B1 | 3/2003 | Visuri et al. |
| 6,544,218 | B1 | 4/2003 | Choi |
| 6,548,010 | B1 | 4/2003 | Stivland et al. |
| 6,560,387 | B1 | 5/2003 | Hehlen et al. |
| 6,607,502 | B1 | 8/2003 | Maguire et al. |
| 6,631,220 | B1 | 10/2003 | Liang et al. |
| 6,652,547 | B2 | 11/2003 | Rabiner et al. |
| 6,666,834 | B2 | 12/2003 | Restle et al. |
| 6,702,781 | B1 | 3/2004 | Reifart et al. |
| 6,773,447 | B2 | 8/2004 | Laguna |
| 6,824,554 | B1 | 11/2004 | Jang |
| 6,849,994 | B1 | 2/2005 | White et al. |
| 6,890,317 | B2 | 5/2005 | Gerdts et al. |
| 6,947,785 | B1 | 9/2005 | Beatty et al. |
| 6,966,890 | B2 | 11/2005 | Coyle et al. |
| 6,978,168 | B2 | 12/2005 | Beatty et al. |
| 6,990,370 | B1 | 1/2006 | Beatty et al. |
| 7,273,470 | B2 | 9/2007 | Wantink |
| 7,309,324 | B2 | 12/2007 | Hayes et al. |
| 7,367,967 | B2 | 5/2008 | Eidenschink |
| 7,470,240 | B2 | 12/2008 | Schultheiss et al. |
| 7,539,231 | B1 | 5/2009 | Honea et al. |
| 7,569,032 | B2 | 8/2009 | Naimark et al. |
| 7,599,588 | B2 | 10/2009 | Eberle et al. |
| 7,641,646 | B2 | 1/2010 | Kennedy, II |
| 7,691,079 | B2 | 4/2010 | Gobel |
| 7,713,260 | B2 | 5/2010 | Lessard |
| 7,758,572 | B2 | 7/2010 | Weber et al. |
| 7,762,984 | B2 | 7/2010 | Kumoyama et al. |
| 7,810,395 | B2 | 10/2010 | Zhou |
| 7,850,685 | B2 | 12/2010 | Kunis et al. |
| 7,867,178 | B2 | 1/2011 | Simnacher |
| 7,909,797 | B2 | 3/2011 | Kennedy, II et al. |
| 7,942,850 | B2 | 5/2011 | Levit et al. |
| 7,967,781 | B2 | 6/2011 | Simpson et al. |
| 7,972,299 | B2 | 7/2011 | Carter |
| 7,985,189 | B1 | 7/2011 | Ogden et al. |
| 8,021,328 | B2 | 9/2011 | Lee |
| 8,029,473 | B2 | 10/2011 | Carter |
| 8,043,256 | B2 | 10/2011 | Hansen |
| 8,066,732 | B2 | 11/2011 | Paul et al. |
| 8,088,121 | B2 | 1/2012 | Nishide |
| 8,157,760 | B2 | 4/2012 | Criado et al. |
| 8,162,859 | B2 | 4/2012 | Schultheiss et al. |
| 8,166,825 | B2 | 5/2012 | Zhou |
| 8,192,368 | B2 | 6/2012 | Woodruff |
| 8,197,505 | B2 | 6/2012 | Hirszowicz et al. |
| 8,246,643 | B2 | 8/2012 | Nita |
| 8,267,886 | B2 | 9/2012 | Ewing |
| 8,292,913 | B2 | 10/2012 | Warnack |
| 8,328,820 | B2 | 12/2012 | Diamant |
| 8,364,235 | B2 | 1/2013 | Kordis et al. |
| 8,372,034 | B2 | 2/2013 | Levit |
| 8,382,738 | B2 | 2/2013 | Simpson et al. |
| 8,414,527 | B2 | 4/2013 | Mallaby |
| 8,419,613 | B2 | 4/2013 | Saadat |
| 8,439,890 | B2 | 5/2013 | Beyar |
| 8,556,813 | B2 | 10/2013 | Cashman et al. |
| 8,556,851 | B2 | 10/2013 | Hirszowicz |
| 8,574,247 | B2 | 11/2013 | Adams et al. |
| 8,657,814 | B2 | 2/2014 | Werneth |
| 8,709,075 | B2 | 4/2014 | Adams et al. |
| 8,728,091 | B2 | 5/2014 | Hakala et al. |

(56) References Cited

U.S. PATENT DOCUMENTS

| | | | |
|---|---|---|---|
| 8,734,424 B2 | 5/2014 | Watanabe | |
| 8,747,416 B2 | 6/2014 | Hakala et al. | |
| 8,784,362 B2 | 7/2014 | Boutilette | |
| 8,834,510 B2 | 9/2014 | Wilson et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 8,986,339 B2 | 3/2015 | Warnack | |
| 8,992,519 B2 | 3/2015 | Kim et al. | |
| 8,992,817 B2 | 3/2015 | Stamberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,011,511 B2 | 4/2015 | Gregorich | |
| 9,044,575 B2 | 6/2015 | Beasley et al. | |
| 9,044,618 B2 | 6/2015 | Hawkins et al. | |
| 9,044,619 B2 | 6/2015 | Hawkins et al. | |
| 9,056,185 B2 | 6/2015 | Fischell et al. | |
| 9,072,534 B2 | 7/2015 | Adams et al. | |
| 9,089,669 B2 | 7/2015 | Haslinger et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,254,169 B2 | 2/2016 | Long et al. | |
| 9,282,984 B2 | 3/2016 | Nita | |
| 9,283,359 B2 | 3/2016 | Pepper | |
| 9,289,132 B2 | 3/2016 | Ghaffari et al. | |
| 9,289,224 B2 | 3/2016 | Adams et al. | |
| 9,289,319 B2 | 3/2016 | Pacetti et al. | |
| 9,320,530 B2 | 4/2016 | Grace | |
| 9,333,000 B2 | 5/2016 | Hakala et al. | |
| 9,339,632 B2 | 5/2016 | Eidenschink et al. | |
| 9,364,645 B2 | 6/2016 | Erikawa | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,433,745 B2 | 9/2016 | Cully | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-Gal | |
| 9,566,209 B2 | 2/2017 | Katragadda et al. | |
| 9,579,114 B2 | 2/2017 | Mantell et al. | |
| 9,579,492 B2 | 2/2017 | Simpson | |
| 9,585,684 B2 | 3/2017 | Nita et al. | |
| 9,592,328 B2 | 3/2017 | Jeevanandam | |
| 9,603,506 B2 | 3/2017 | Goldfarb et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,700,655 B2 | 7/2017 | Laudenslager et al. | |
| 9,730,715 B2 | 8/2017 | Adams | |
| 9,737,361 B2 | 8/2017 | Magana | |
| 9,764,142 B2 | 9/2017 | Imran | |
| 9,782,570 B2 | 10/2017 | Hirszowicz | |
| 9,814,476 B2 | 11/2017 | Adams et al. | |
| 9,833,348 B2 | 12/2017 | Jordan et al. | |
| 9,839,764 B2 | 12/2017 | Chouinard | |
| 9,861,377 B2 | 1/2018 | Mantell et al. | |
| 9,867,629 B2 | 1/2018 | Hawkins et al. | |
| 9,878,135 B2 | 1/2018 | Holzapfel et al. | |
| 9,894,756 B2 | 2/2018 | Weinkam et al. | |
| 9,901,704 B2 | 2/2018 | Appling | |
| 9,955,946 B2 | 5/2018 | Miller et al. | |
| 9,974,963 B2 | 5/2018 | Imran | |
| 9,974,970 B2 | 5/2018 | Nuta et al. | |
| 9,993,292 B2 | 6/2018 | Adams et al. | |
| 10,039,561 B2 | 8/2018 | Adams et al. | |
| 10,076,384 B2 | 9/2018 | Kasprzyk | |
| 10,086,175 B2 | 10/2018 | Torres et al. | |
| 10,124,153 B2 | 11/2018 | Feig | |
| 10,136,829 B2 | 11/2018 | Deno et al. | |
| 10,149,690 B2 | 12/2018 | Hawkins et al. | |
| 10,159,505 B2 | 12/2018 | Hakala et al. | |
| 10,194,994 B2 | 2/2019 | Deno et al. | |
| 10,201,387 B2 | 2/2019 | Grace et al. | |
| 10,206,698 B2 | 2/2019 | Hakala et al. | |
| 10,226,265 B2 | 3/2019 | Ku et al. | |
| 10,245,410 B2 | 4/2019 | Aggerholm | |
| 10,327,846 B1 | 6/2019 | Stark et al. | |
| 10,328,290 B2 | 6/2019 | Zhou et al. | |
| 10,357,264 B2 | 7/2019 | Kat-Kuoy | |
| 10,405,923 B2 | 9/2019 | Yu et al. | |
| 10,406,031 B2 | 9/2019 | Thyzel | |
| 10,406,318 B2 | 9/2019 | Williams | |
| 10,420,569 B2 | 9/2019 | Adams | |
| 10,439,791 B2 | 10/2019 | Kalhan | |
| 10,441,300 B2 | 10/2019 | Hawkins | |
| 10,449,339 B2 | 10/2019 | Wilson et al. | |
| 10,463,430 B2 | 11/2019 | Dick | |
| 10,478,202 B2 | 11/2019 | Adams et al. | |
| 10,517,620 B2 | 12/2019 | Adams | |
| 10,517,621 B1 | 12/2019 | Hakala et al. | |
| 10,537,287 B2 | 1/2020 | Braido et al. | |
| 10,555,744 B2 | 2/2020 | Nguyen et al. | |
| 10,561,428 B2 | 2/2020 | Eggert et al. | |
| 10,583,277 B2 | 3/2020 | Rundquist | |
| 10,589,073 B2 | 3/2020 | Mallaby | |
| 10,617,850 B2 | 4/2020 | Tal | |
| 10,646,240 B2 | 5/2020 | Betelia et al. | |
| 10,668,245 B2 | 6/2020 | Kanae | |
| 10,682,178 B2 | 6/2020 | Adams et al. | |
| 10,695,531 B2 | 6/2020 | Suzuki | |
| 10,702,293 B2 | 7/2020 | Adams et al. | |
| 10,709,462 B2 | 7/2020 | Nguyen et al. | |
| 10,709,872 B2 | 7/2020 | Alvarez et al. | |
| 10,758,255 B2 | 9/2020 | Adams | |
| 10,797,684 B1 | 10/2020 | Benz et al. | |
| 10,799,688 B2 | 10/2020 | Calhoun | |
| 10,842,567 B2 | 11/2020 | Grace et al. | |
| 10,850,075 B2 | 12/2020 | Tarunaga | |
| 10,857,329 B2 | 12/2020 | Davies | |
| 10,933,225 B2 | 3/2021 | Campbell | |
| 10,952,740 B2 | 3/2021 | Dasnurkar et al. | |
| 10,952,790 B2 | 3/2021 | Haverkost et al. | |
| 10,959,743 B2 | 3/2021 | Adams et al. | |
| 10,966,737 B2 | 4/2021 | Nguyen | |
| 10,967,156 B2 | 4/2021 | Gulachenski | |
| 10,973,538 B2 | 4/2021 | Hakala et al. | |
| 10,974,028 B2 | 4/2021 | Buller et al. | |
| 10,980,987 B2 | 4/2021 | Tarunaga | |
| 11,000,299 B2 | 5/2021 | Hawkins et al. | |
| 11,020,135 B1 | 6/2021 | Hawkins | |
| 11,026,707 B2 | 6/2021 | Ku et al. | |
| 11,040,176 B2 | 6/2021 | Blanchard et al. | |
| 11,058,492 B2 | 7/2021 | Grace et al. | |
| 11,076,874 B2 | 8/2021 | Hakala et al. | |
| 11,116,939 B2 | 9/2021 | Jamous et al. | |
| 11,141,131 B2 | 10/2021 | Stigall | |
| 11,179,169 B2 | 11/2021 | Brouillete et al. | |
| 11,207,493 B2 | 12/2021 | Suzuki et al. | |
| 11,213,661 B2 | 1/2022 | Spindler | |
| 11,229,772 B2 | 1/2022 | Nita | |
| 11,229,776 B2 | 1/2022 | Kugler et al. | |
| 11,246,659 B2 | 2/2022 | Grace et al. | |
| 11,253,681 B2 | 2/2022 | Williams | |
| 11,266,817 B2 | 3/2022 | Cope et al. | |
| 11,389,171 B2 | 7/2022 | Goldsmith | |
| 11,389,628 B2 | 7/2022 | Spencer | |
| 11,395,669 B2 | 7/2022 | O'Malley et al. | |
| 11,399,862 B2 | 8/2022 | Massimini et al. | |
| 11,406,452 B2 | 8/2022 | Efremkin | |
| 11,406,799 B2 | 8/2022 | McEvaddy et al. | |
| 11,484,327 B2 | 11/2022 | Anderson et al. | |
| 11,540,848 B2 | 1/2023 | Cai et al. | |
| 11,564,729 B2 | 1/2023 | Walzman | |
| 11,602,363 B2 | 3/2023 | Nguyen | |
| 11,633,200 B2 | 4/2023 | Anderson et al. | |
| 11,672,585 B2 | 6/2023 | Schultheis | |

(56) References Cited

U.S. PATENT DOCUMENTS

| | | |
|---|---|---|
| 11,672,599 B2 | 6/2023 | Schultheis et al. |
| 11,707,323 B2 | 7/2023 | Schultheis et al. |
| 11,771,449 B2 | 10/2023 | Adams et al. |
| 11,779,363 B2 | 10/2023 | Vo |
| 11,826,530 B2 | 11/2023 | Suzuki |
| 11,839,391 B2 | 12/2023 | Schultheis et al. |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |
| 11,950,793 B2 | 4/2024 | Nguyen |
| 12,011,185 B2 | 6/2024 | Vo |
| 12,023,098 B2 | 7/2024 | Nguyen |
| 12,035,932 B1 | 7/2024 | Nunes |
| 12,076,077 B2 | 9/2024 | Mori |
| 12,144,516 B2 | 11/2024 | Betelia |
| 12,178,458 B1 | 12/2024 | Betelia et al. |
| 12,193,691 B2 | 1/2025 | Adams |
| 2001/0016761 A1 | 8/2001 | Rudie |
| 2001/0018569 A1 | 8/2001 | Erbel |
| 2001/0020164 A1* | 9/2001 | Papademetriou .... G02B 6/3636 606/7 |
| 2001/0049464 A1 | 12/2001 | Ganz |
| 2001/0051784 A1 | 12/2001 | Brisken |
| 2002/0045811 A1 | 4/2002 | Kittrell et al. |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Jebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0142703 A1 | 6/2006 | Carter |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142779 A1 | 6/2007 | Duane |
| 2007/0142819 A1 | 6/2007 | El-Nounou et al. |
| 2007/0142821 A1 | 6/2007 | Hennessy et al. |
| 2007/0142856 A1 | 6/2007 | Jang |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036238 A1 | 2/2010 | Neidert |
| 2010/0036294 A1 | 2/2010 | Mantell et al. |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0286791 A1 | 11/2010 | Goldsmith |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |

(56) References Cited

U.S. PATENT DOCUMENTS

| | | |
|---|---|---|
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0323211 A1 | 12/2012 | Ogle |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0060234 A1 | 3/2013 | Besser |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 2/2014 | Diodone et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1* | 4/2014 | Sawada ............... G02B 6/3878 |
| | | 600/478 |
| 2014/0128848 A1 | 5/2014 | Appling et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |
| 2014/0336626 A1 | 11/2014 | Jiang |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0071591 A1* | 3/2015 | Chen .................... G02B 6/3873 |
| | | 385/72 |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0342681 A1 | 12/2015 | Lee |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0234534 A1 | 8/2016 | Kitahara et al. |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0324564 A1 | 11/2016 | Gerlach et al. |
| 2016/0331389 A1 | 11/2016 | Hakala et al. |
| 2016/0339204 A1 | 11/2016 | Williams |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 5/2018 | Thumpudi et al. |
| 2018/0169392 A1 | 6/2018 | Franklin |
| 2018/0214677 A1 | 8/2018 | Tarunaga |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |

(56) References Cited

U.S. PATENT DOCUMENTS

| | | |
|---|---|---|
| 2019/0150960 A1 | 5/2019 | Nguyen et al. |
| 2019/0150961 A1 | 5/2019 | Tozzi |
| 2019/0159792 A1 | 5/2019 | Panian |
| 2019/0167349 A1 | 6/2019 | Shamay |
| 2019/0175111 A1 | 6/2019 | Genereux et al. |
| 2019/0175300 A1 | 6/2019 | Horn et al. |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0285803 A1 | 9/2019 | Van Zuylen |
| 2019/0321100 A1 | 10/2019 | Masotti et al. |
| 2019/0321101 A1 | 10/2019 | Massoti et al. |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2019/0388654 A1 | 12/2019 | Chou |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0345380 A1 | 11/2020 | Boyle et al. |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0001138 A1 | 1/2022 | Howell |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0040454 A1 | 2/2022 | Hamm |
| 2022/0054194 A1 | 2/2022 | Bacher et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0249166 A1 | 8/2022 | Cook et al. |
| 2022/0273324 A1 | 9/2022 | Schultheis |
| 2022/0287732 A1 | 9/2022 | Anderson et al. |
| 2022/0313293 A1 | 10/2022 | Singh |
| 2022/0313359 A1 | 10/2022 | Schultheis et al. |
| 2022/0338890 A1 | 10/2022 | Anderson et al. |
| 2022/0354578 A1 | 11/2022 | Cook |
| 2022/0387106 A1 | 12/2022 | Cook |
| 2023/0013920 A1 | 1/2023 | Massimini |
| 2023/0064371 A1 | 3/2023 | Cook et al. |
| 2023/0137107 A1 | 5/2023 | Cook et al. |
| 2023/0157754 A1 | 5/2023 | Bacher et al. |
| 2023/0200906 A1 | 6/2023 | Cook et al. |
| 2023/0233256 A1 | 7/2023 | Cook et al. |
| 2023/0240748 A1 | 8/2023 | Cook et al. |
| 2023/0248376 A1 | 8/2023 | Anderson et al. |
| 2023/0255635 A1 | 8/2023 | Schultheis et al. |
| 2023/0255688 A1 | 8/2023 | Schultheis et al. |
| 2023/0255689 A1 | 8/2023 | Schultheis et al. |
| 2023/0310054 A1 | 10/2023 | Schultheis |
| 2023/0310067 A1 | 10/2023 | Schultheis et al. |
| 2023/0310073 A1 | 10/2023 | Adams et al. |
| 2023/0320576 A1 | 10/2023 | Feldman |
| 2023/0338088 A1 | 10/2023 | Massimini et al. |
| 2023/0338089 A1 | 10/2023 | Schultheis |
| 2023/0414234 A1 | 12/2023 | Anderson et al. |
| 2024/0001076 A1 | 1/2024 | Gelsinger |
| 2024/0016508 A1 | 1/2024 | Kocur |
| 2024/0016544 A1 | 1/2024 | Schultheis et al. |
| 2024/0016545 A1 | 1/2024 | Schultheis et al. |
| 2024/0023813 A1 | 1/2024 | Milner |
| 2024/0032995 A1 | 2/2024 | Schultheis et al. |
| 2024/0033002 A1 | 2/2024 | Cook |
| 2024/0041520 A1 | 2/2024 | Schultheis et al. |
| 2024/0050170 A1 | 2/2024 | Fournier |
| 2024/0050696 A1 | 2/2024 | Japuntich |
| 2024/0058060 A1 | 2/2024 | Cook et al. |
| 2024/0065711 A1 | 2/2024 | Hendrickson |
| 2024/0065712 A1 | 2/2024 | Schultheis |
| 2024/0099773 A1 | 3/2024 | Schabert |
| 2024/0122648 A1 | 4/2024 | Cook |
| 2024/0165658 A1 | 5/2024 | Fu |
| 2024/0173044 A1 | 5/2024 | Chen et al. |
| 2024/0173526 A1 | 5/2024 | Kofidis |
| 2024/0189543 A1 | 6/2024 | Salinas |

(56)  References Cited

U.S. PATENT DOCUMENTS

| 2024/0216062 A1 | 7/2024 | Cook |
| 2024/0260981 A1 | 8/2024 | Betelia |
| 2024/0260982 A1 | 8/2024 | Peterson |
| 2024/0277410 A1 | 8/2024 | Cook |
| 2024/0277974 A1 | 8/2024 | Oehler |
| 2024/0277980 A1 | 8/2024 | O'Neill |
| 2024/0285296 A1 | 8/2024 | Vo |
| 2024/0285922 A1 | 8/2024 | Chu |
| 2024/0299051 A1 | 9/2024 | Sidhu et al. |
| 2024/0307119 A1 | 9/2024 | Nguyen |
| 2024/0325045 A1 | 10/2024 | Otake |
| 2024/0382258 A1 | 11/2024 | Schultheis |
| 2025/0025237 A1 | 1/2025 | Cook |
| 2025/0040947 A1 | 2/2025 | Schultheis |

FOREIGN PATENT DOCUMENTS

| AU | 2022227829 | 9/2022 |
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 113993463 | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| CN | 117752412 | 3/2024 |
| CN | 118055734 | 5/2024 |
| DE | 3038445 A1 | 5/1982 |
| DE | 3836337 A1 | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 0547146 | 7/1995 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2470248 | 7/2012 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 2961463 | 5/2019 |
| EP | 3240603 | 5/2019 |
| EP | 3197381 | 3/2020 |
| EP | 3643260 A1 | 4/2020 |
| EP | 3240494 | 3/2021 |
| EP | 3522812 | 12/2021 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| EP | 4277537 | 11/2023 |
| EP | 4297669 | 1/2024 |
| EP | 4146322 | 4/2024 |
| EP | 3182931 | 6/2024 |
| EP | 3950036 | 8/2024 |
| EP | 4034005 | 12/2024 |
| GB | 1082397 | 9/1967 |
| JP | S62275446 A | 11/1987 |
| JP | H05264763 | 10/1993 |
| JP | 1996089511 | 4/1996 |
| JP | H08-114724 A | 5/1996 |
| JP | H09117407 | 5/1997 |
| JP | 2001520070 | 10/2001 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2012505050 | 3/2012 |
| JP | 2014123147 | 7/2014 |
| JP | A2014516614 | 7/2014 |
| JP | A2015522344 | 8/2015 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | WO9524867 | 9/1995 |
| WO | 1999002095 A1 | 1/1999 |
| WO | 1999020189 A1 | 4/1999 |
| WO | WO200067648 | 11/2000 |
| WO | WO2000067648 A1 | 11/2000 |
| WO | WO0103599 | 1/2001 |
| WO | WO0103599 A2 | 1/2001 |
| WO | 20060006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 20110126580 A2 | 10/2011 |
| WO | WO2011126580 A3 | 10/2011 |
| WO | WO2012025833 | 3/2012 |
| WO | WO2012042619 | 4/2012 |
| WO | WO20120052924 A1 | 4/2012 |

(56)    References Cited

FOREIGN PATENT DOCUMENTS

| | | |
|---|---|---|
| WO | WO2012058156 | 5/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 A1 | 6/2021 |
| WO | WO2021150502 A1 | 7/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |
| WO | WO2024079108 | 4/2024 |
| WO | WO2024107418 | 5/2024 |

OTHER PUBLICATIONS

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

(56) References Cited

OTHER PUBLICATIONS

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers In Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and On Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser Induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method For Fabricating Artificial Kidney Stones Of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

"Custom Medical Skived Tubing", Duke Extrusion, 2025. https://www.dukeextrusion.com/tubing-options/skived-tubing.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCI excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

(56) References Cited

OTHER PUBLICATIONS

Deckelbaum, L., "Coronary Laser Angioplasty", Lasers in Surgery and Medicine, 1994, pp. 101-110, vol. 14, Wiley-Liss Inc., Conneticuit, USA.

Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.

Varghese, B., et al. "Influence of absorption induced thermal initiation pathway on irradiance threshold for laser Induced breakdown", Biomedical Optics Express, 2015, vol. 6, No. 4, Optical Society of America.

Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

European Search Report, for European Application No. 18185152, mailed Dec. 13, 2018.

International Search Report and Written Opinion dated May 22, 2019, in PCT Application Serial No. PCT/US2019/022009.

International Search Report and Written Opinion dated May 29, 2019, in PCT Application Serial No. PCT/US2019/022016.

International Search Report and Written Opinion dated Jun. 22, 2018, in Application Serial No. NL2019807, issued by the European Patent Office.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, mailed Jan. 16, 2019.

European Search Report, for European Patent Application No. 18185152.8, mailed Dec. 20, 2018.

International Search Report and Written Opinion dated Jul. 29, 2020 in PCT Application Serial No. PCT/US2020/034005.

International Search Report and Written Opinion dated Sep. 11, 2020 in PCT Application Serial No. PCT/US2020/038517.

International Search Report and Written Opinion dated Sep. 9, 2020 in PCT Application Serial No. PCT/US2020/038530.

International Search Report and Written Opinion dated Sep. 11, 2020 in PCT Application Serial No. PCT/US2020/038521.

International Search Report and Written Opinion dated Sep. 7, 2020 in PCT Application Serial No. PCT/US2020/034642.

Shen, Yajie et al. "High-peak-power and narrow-linewidth Q-switched Ho: YAG laser in-band pumped at 1931 nm." Applied Physics Express 13.5 (2020): 052006. (Year 2020).

International Search Report and Written Opinion dated Aug. 25, 2022 in PCT Application Serial No. PCTUS/2022/028035.

International Search Report and Written Opinion dated Sep. 15, 2022 in PCT Application Serial No. PCTUS/2022/032045.

AccuCoat, "Beamsplitter: Divide, combine & conquer"; 2023.

Lin et al., "Photoacoustic imaging", Science Direct; 2021.

Zhou et al., "Photoacoustic Imaging with fiber optic technology: A review", Science Direct; 2020.

International Search Report and Written Opinion issued by the European Patent Office, for Serial No. PCT/US2022/053775, dated Apr. 21, 2023. (Re 45PCT).

International Search Report and Written Opinion issued by the European Patent Office, for Serial No. PCT/US2023/011497, dated Apr. 28, 2023. (Re 54PCT).

International Search Report and Written Opinion issued by the European Patent Office, for Serial No. PCT/US2023/012599, dated May 19, 2023. (Re 57PCT).

PathFinder Digital, "Free Space Optics vs. Fiber Optics", 2023.

International Search Report and Written Opinion, issued in Application Serial No. PCT/US2023/016152, dated Jul. 12, 2023.

International Preliminary Report on Patentability dated Sep. 15, 2020 in PCT Application Serial No. PCT/US2019/022009.

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

Schafter+Kirchhoff, Laser Beam Couplers series 60SMS for coupling into single-mode and polarization- maintaining fiber cables, Schafter+Kirchhoff, pp. 1-5, Germany. Dec. 2, 2021.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

Partial Search Report and Provisional Opinion dated Feb. 19, 2021 in PCT Application Serial No. PCT/US2020/059960.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation. Diss. Queen's University (Canada), 2016.

Meng et al., "Accurate Recovery Of Atrial Endocardial Potential Maps From Non-contact Electrode Data." Auckland Bioengineering Institute. (ID 1421). May 2019.

Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.

Sacher et al., "Comparison Of Manual Vs Automatic Annotation To Identify Abnormal Substrate For Scar Related VT Ablation." LIRYC

(56) References Cited

OTHER PUBLICATIONS

Institute, Bordeaux University Hospital, France (ID 1336). Poster for conference in San Francisco, May 8-11, 2019.

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Aug. 20, 2021 in PCT Application Serial No. PCT/US2021/031130.

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

International Search Report and Written Opinion, PCT Application Serial No. PCT/US2022/047751 issued Feb. 10, 2023, by the European Patent Office. (56PCT).

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

McAteer, James A., et al. "Ultracal-30 Gypsum Artificial Stones For Research On The Mechinisms Of Stone Breakage In Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland. 2015.

Medlight, "Cylindircal light diffuser Model RD", Medlight S.A., Switzerland. 2015.

Mayo, Michael E., "Interaction of Laser Radiation with Urinary Calculi", Cranfield University Defense and Security, PhD Thesis, 2009, Cranfield University.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'Nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing. Oct. 2015.

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologics, 2014, Pinnacle Biologics, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

(56) References Cited

OTHER PUBLICATIONS

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion, issued by the EP/ISA, in PCT/US2021/048819, dated Jan. 14, 2022.

International Search Report and Written Opinion dated Nov. 8, 2022 in PCT Application Serial No. PCTUS/2022/039678.

Definition of ablation—NCI Dictionary of Cancer Terms—NCI, National Cancer Institute, p. 1 (Year:2025).

Daemen, J., Tovar Forero, M.N, "The Coronary Intravascular Lithotripsy System", ICR Journal, 2019; 14(3); 174-181.

Butt, N., Khalid, N., Shlofmitz, E., "Intravascular Lithotripsy"; NCBI Bookshelf. A service of the National Library of Medicine, National Institutes of Health; StatPearls Publishing, 2023.

* cited by examiner

CONNECTOR FOR MULTIPLEXER OPTICAL COUPLING

RELATED APPLICATION

This application is related to and claims priority on U.S. Provisional Patent Application Ser. No. 63/236,633 filed on Aug. 24, 2021, and entitled "CONNECTOR FOR MULTIPLEXER OPTICAL COUPLING." To the extent permissible, the contents of U.S. Provisional Application Ser. No. 63/236,633 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a catheter system for treating a treatment site within or adjacent to a vessel wall or a heart valve. In various embodiments, the catheter system includes a light source, a first light guide, a second light guide, and a guide bundle. The light source generates light energy. The first light guide receives the light energy from the light source. The first light guide has a guide proximal end. The second light guide receives the light energy from the light source. The second light guide has a guide proximal end. A guide bundle is in optical communication with the light source. The guide bundle bundles the first light guide and the second light guide. The guide bundle includes a first ferrule that engages the guide proximal end of the first light guide, and a second ferrule that engages the guide proximal end of the second light guide.

In some embodiments, the guide bundle further includes (i) a first ferrule assembly including the first ferrule, and (ii) a second ferrule assembly including the second ferrule.

In certain embodiments, at least one of the first ferrule and the second ferrule are formed at least partially from a ceramic material.

In various embodiments, at least one of the first ferrule and the second ferrule are formed at least partially from a metallic material.

In some embodiments, the first ferrule assembly further includes a first spring that engages the first ferrule and the second ferrule assembly further includes a second spring that engages the second ferrule.

In certain embodiments, the catheter system further includes a receptacle assembly that receives the first ferrule and the second ferrule.

In various embodiments, the receptacle assembly is formed at least partially from a ceramic material.

In some embodiments, the receptacle assembly is formed at least partially from a metallic material.

In certain embodiments, the receptacle assembly includes at least one alignment guide that is configured to guide the alignment of the receptacle assembly and the guide bundle.

In various embodiments, the alignment guide is a guide pin.

In some embodiments, the alignment guide is a guide tongue of a tongue and groove system.

In certain embodiments, the alignment guide is a guide rail.

In various embodiments, the receptacle assembly includes a receptacle block that is coupled to a backing plate, the backing plate being configured to engage the first ferrule and the second ferrule.

In some embodiments, each of the ferrules includes a proximal end face, and wherein the backing plate is configured to engage each of the proximal end faces.

In certain embodiments, the backing plate includes (i) a first alignment hole that is configured to align a first guide beam with the first light guide, and (ii) a second alignment hole that is configured to align a second guide beam with the second light guide.

In various embodiments, the receptacle assembly includes (i) a first receptacle hole that is configured to receive the first ferrule, and (ii) a second receptacle hole that is configured to receive the second ferrule.

In some embodiments, the first receptacle hole and the second receptacle hole are each formed in the receptacle block, the first receptacle hole and the second receptacle hole being aligned on a same linear axis as one another.

In certain embodiments, the first receptacle hole and the second receptacle hole are each formed in the receptacle block as v-grooves.

In various embodiments, the receptacle assembly includes a retainer assembly that retains (i) the first ferrule in the first receptacle hole, and (ii) the second ferrule in the second receptacle hole.

In some embodiments, the retainer assembly includes a clamping bar having a ball spring plunger, the ball spring plunger being configured to contact (i) at least a portion of the first ferrule so that the first ferrule is retained in the first receptacle hole, and (ii) at least a portion of the second ferrule so that the second ferrule is retained in the second receptacle hole.

In certain embodiments, the clamping bar is configured to be rotatable about a clamping bar axis.

In various embodiments, the clamping bar includes a compliant material that is configured to spread a retaining force across the ferrules so that each of the ferrules is retained within a corresponding receptacle hole.

The present invention is also directed toward a method for treating a vascular lesion within or adjacent to a vessel wall using the catheter system of any of the embodiments described herein.

The present invention is further directed toward a method for manufacturing the catheter system of any of the embodiments described herein.

The present invention is also directed toward a catheter system for treating a treatment site within or adjacent to a vessel wall or a heart valve. In various embodiments, the catheter system includes a light source, a plurality of light guides, a guide bundle, and a receptacle assembly. The light source generates light energy. The plurality of light guides each individually receives the light energy from the light source. Each of the plurality of light guides has a corresponding guide proximal end. The guide bundle is in optical communication with the light source. The guide bundle bundles the plurality of light guides. The guide bundle includes a plurality of ferrules that each engages one of the guide proximal ends of a corresponding light guide. The receptacle assembly receives and aligns the plurality of ferrules into one of (i) a circular pattern, and (ii) a hexagonal pattern.

In some embodiments, at least one of the light guides is an optical fiber.

In certain embodiments, the light source is a laser.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include but are not limited to, major adverse cardiac events, major adverse events in the peripheral or central vasculature, major adverse events in the brain, major adverse events in the musculature, or major adverse events in any of the internal organs.

As used herein, the terms "intravascular lesion", "vascular lesion" and "treatment site" are used interchangeably unless otherwise noted. The intravascular lesions and/or the vascular lesions are sometimes referred to herein simply as "lesions". Also, as used herein, the terms "focused location" and "focused spot" can be used interchangeably unless otherwise noted and can refer to any location where the light energy is focused to a small smaller diameter than the initial diameter of the light source.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

Figure 1:
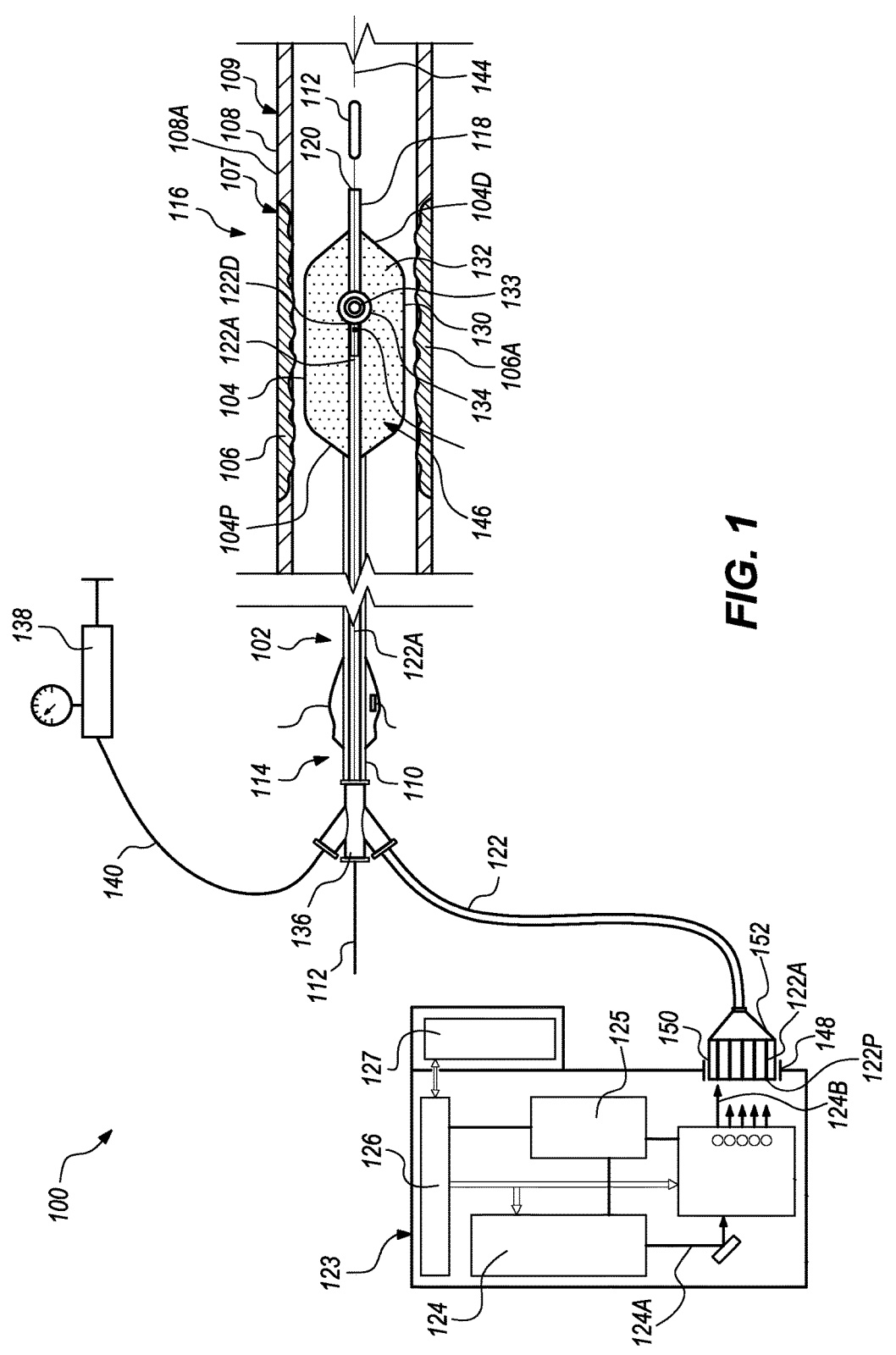
FIG. 1 is a simplified, cross-sectional view of an embodiment of a catheter system in accordance with various embodiments herein, the catheter system including a multiplexer and a guide bundle having features of the present invention.

The catheter systems disclosed herein can include many different forms. Referring now to FIG. 1, a schematic cross-sectional view is shown of a catheter system 100 in accordance with various embodiments. The catheter system 100 is suitable for imparting pressure waves to induce fractures in one or more treatment sites within or adjacent to a vessel wall of a blood vessel, or on or adjacent to a heart valve, within a body of a patient. In the embodiment illustrated in FIG. 1, the catheter system 100 can include one or more of a catheter 102, an energy guide bundle 122 including one or more energy guides 122A (some embodiments described here include at least a first energy guide and a second energy guide), a source manifold 136, a fluid pump 138, a multiplexer 123 including one or more of an energy source 124, a power source 125, a system controller 126, and a graphic user interface 127 (a "GUI"), and a handle assembly 128. Alternatively, the catheter system 100 can include more components or fewer components than those specifically illustrated and described in relation to FIG. 1.

It is appreciated that in some embodiments the energy guide bundle 122 shown and described can be a light guide bundle 122, which can include one or more light guides 122A. In certain embodiments, the energy source 124 can include a light source 124. For example, the energy guides 122A can be optical fibers, and/or the energy source 124 can include a laser. Alternatively, the energy guide bundle 122 can include different types of energy guides 122A (such as electrodes or electrode pairs), and/or a different type of energy source 124 (such as a high voltage energy source, for example). It is understood that the energy guides 122A and/or the energy source 124 can include any suitable type of energy guides or energy sources that can generate and/or transmit energy.

In various embodiments, the catheter 102 is configured to move to a treatment site 106 within or adjacent to a vessel wall 108A of a blood vessel 108 within a body 107 of a patient 109. The treatment site 106 can include one or more vascular lesions 106A such as calcified vascular lesions, for example. Additionally, or in the alternative, the treatment site 106 can include vascular lesions 106A such as fibrous vascular lesions. Still alternatively, in some implementations, the catheter 102 can be used at a treatment site 106 within or adjacent to a heart valve within the body 107 of the patient 109.

The catheter 102 can include an inflatable balloon 104 (sometimes referred to herein simply as a "balloon"), a catheter shaft 110, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. As utilized herein, the guidewire lumen 118 defines a conduit through which the guide wire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a balloon fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment sites 106. It is appreciated that although FIG. 1 illustrates the balloon wall 130 of the balloon 104 is shown spaced apart from the treatment site 106 of the blood vessel 108 when in the inflated state, this is done merely for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloon 104 is made from silicone. In other embodiments, the balloon 104 can be made from polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloons 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be used for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug eluting coating or a drug eluting stent structure. The drug eluting coating or drug eluting stent can include one or more therapeutic agents including anti-inflammatory agents, antineoplastic agents, anti-angiogenic agents, and the like.

The balloon fluid 132 can be a liquid or a gas. Some examples of the balloon fluid 132 suitable for use can include, but are not limited to one or more of water, saline, contrast medium, fluorocarbons, perfluorocarbons, gases, such as carbon dioxide, or any other suitable balloon fluid 132. In some embodiments, the balloon fluid 132 can be used as a base inflation fluid. In some embodiments, the balloon fluid 132 can include a mixture of saline to contrast medium in a volume ratio of approximately 50:50. In other embodiments, the balloon fluid 132 can include a mixture of saline to contrast medium in a volume ratio of approximately 25:75. In still other embodiments, the balloon fluid 132 can include a mixture of saline to contrast medium in a volume ratio of approximately 75:25. However, it is understood that any suitable ratio of saline to contrast medium can be used. The balloon fluid 132 can be tailored on the basis of composition, viscosity, and the like so that the rate of travel of the pressure waves are appropriately manipulated. In certain embodiments, the balloon fluid 132 suitable for use herein is biocompatible. A volume of balloon fluid 132 can be tailored by the chosen light source 124 and the type of balloon fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as perfluorocarbon dode-cafluoropentane (DDFP, C5F12).

The balloon fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the balloon fluid 132 can include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG—emission maximum=1064 nm) lasers, holmium: YAG (Ho:YAG—emission maximum=2.1 μm) lasers, or erbium:YAG (Er:YAG—emission maximum=2.94 μm) lasers. In some embodiments, the absorptive agents can be water soluble. In other embodiments, the absorptive agents are not water soluble. In some embodiments, the absorptive agents used in the balloon fluids 132 can be tailored to match the peak emission of the light source 124. Various light sources 124 having emission wavelengths of at least ten nanometers to one millimeter are discussed elsewhere herein.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. Each of the light guides 122A can have a guide distal end 122D that is at any suitable longitudinal position relative to a length of the balloon 104. In some embodiments, each light guide 122A can be an optical fiber, and the light source 124 can be a laser. The light source 124 can be in optical communication with the light guides 122A at the proximal portion 114 of the catheter system 100. More particularly, the light source 124 can selectively, simultaneously, sequentially, and/or be in optical communication with each of the light guides 122A in any desired combination, order, and/or pattern due to the presence and operation of the multiplexer 128.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110, or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, the light guides 122A can be disposed either uniformly or non-uniformly about the guidewire lumen 118 and/or the catheter shaft 110 to achieve the desired effect in the desired locations.

The catheter system 100 and/or the light guide bundle 122 can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A can have any suitable design for purposes of generating plasma and/or pressure waves in the balloon fluid 132 within the balloon interior 146. In certain embodiments, the light guides 122A can include an optical fiber or flexible light pipe. The light guides 122A can be thin and flexible and can allow light signals to be sent with very little loss of strength. The light guides 122A can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light energy along its length from a guide proximal end 122P to the guide distal end 122D having at least one optical window (not shown) that is positioned within the balloon interior 146.

The light guides 122A can assume many configurations about and/or relative to the catheter shaft 110 of the catheter 102. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A can be disposed within one or more light guide lumens within the catheter shaft 110.

The light guides 122A can also be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the light guides 122A can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. The direction of the acoustic wave can be tailored by changing an angle of the guide distal end 122D of the light guide 122A.

In certain embodiments, the photoacoustic transducers 154 disposed at the guide distal end 122D of the light guide 122A can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The light guide 122A can further include additional photoacoustic transducers 154 disposed along one or more side surfaces of the length of the light guide 122A.

In some embodiments, the light guides 122A can further include one or more diverting features or "diverters" (not shown in FIG. 1) within the light guide 122A that are configured to direct light to exit the light guide 122A toward a side surface which can be located at or near the guide distal end 122D of the light guide 122A, and toward the balloon wall 130. A diverting feature can include any feature of the system that diverts light energy from the light guide 122A away from its axial path toward a side surface of the light guide 122A. Additionally, the light guides 122A can each include one or more light windows disposed along the longitudinal or circumferential surfaces of each light guide 122A and in optical communication with a diverting feature. Stated in another manner, the diverting features can be configured to direct light energy in the light guide 122A toward a side surface that is at or near the guide distal end 122D, where the side surface is in optical communication with a light window. The light windows can include a portion of the light guide 122A that allows light energy to exit the light guide 122A from within the light guide 122A, such as a portion of the light guide 122A lacking a cladding material on or about the light guide 122A.

Examples of the diverting features suitable for use include a reflecting element, a refracting element, and a fiber diffuser. The diverting features suitable for focusing light energy away from the tip of the light guides 122A can include but are not to be limited to, those having a convex surface, a gradient-index (GRIN) lens, and a mirror focus lens. Upon contact with the diverting feature, the light energy is diverted within the light guide 122A to one or more of a plasma generator 133 and the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the one or more light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132 as needed.

As noted above, in the embodiment illustrated in FIG. 1, the multiplexer 123 includes one or more of the light source 124, the power source 125, the system controller 126, and the GUI 127. Alternatively, the multiplexer 123 can include more components or fewer components than those specifically illustrated in FIG. 1. For example, in certain non-exclusive alternative embodiments, the multiplexer 123 can be designed without the GUI 127. Still alternatively, one or more of the light source 124, the power source 125, the system controller 126, and the GUI 127 can be provided within the catheter system 100 without the specific need for the multiplexer 123.

In some embodiments, the multiplexer 123 can include a two-channel splitter design. The light guide bundle 122 can include a manual positioning mechanism that is mounted on an optical breadboard and/or platen. This design enables linear positional adjustment and array tilting by rotating about a channel one light guide 122A axis (not shown in FIG. 1). The adjustment method, in other embodiments, can include at least two adjustment steps, 1) aligning the planar positions of the source beam 124B at Channel 1, and 2) adjusting the light guide bundle 122 to achieve the best alignment at Channel 10.

As shown, the multiplexer 123, and the components included therewith, is operatively coupled to the catheter 102, the light guide bundle 122, and the remainder of the catheter system 100. For example, in some embodiments, as illustrated in FIG. 1, the multiplexer 123 can include a console connection aperture 148 (also sometimes referred to generally as a "socket") by which the light guide bundle 122 is mechanically coupled to the multiplexer 123. In such embodiments, the light guide bundle 122 can include a guide coupling housing 150 that houses a portion, e.g., the guide proximal end 122P, of each of the light guides 122A. The guide coupling housing 150 is configured to fit and be selectively retained within the console connection aperture 148 to provide the mechanical coupling between the light guide bundle 122 and the multiplexer 123.

The light guide bundle 122 can also include a guide bundle 152 (or "shell") that brings each of the individual light guides 122A closer together so that the light guides 122A and/or the light guide bundle 122 can be in a more compact form as it extends with the catheter 102 into the blood vessel 108 during use of the catheter system 100. In some embodiments, the light guides 122A leading to the plasma generator 133 can be organized into a light guide bundle 122 including a linear block with an array of precision holes forming a multi-channel ferrule 778 (illustrated in FIG. 7, for example). In other embodiments, the light guide bundle 122 could include a mechanical connector array or block connector that organizes singular ferrules 778 into one of (i) a linear array, (ii) a circular pattern, and (iii) a hexagonal pattern.

The light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, such as a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122. The light source 124 can be operated at low energies.

The light source 124 can have any suitable design. In certain embodiments, the light source 124 can be configured to provide sub-millisecond pulses of light energy from the light source 124 that are focused onto a small spot in order to couple it into the guide proximal end 122P of the light guide 122A. Such pulses of light energy are then directed and/or guided along the light guides 122A to a location within the balloon interior 146 of the balloon 104, thereby inducing plasma formation (also sometimes referred to herein as a "plasma flash") in the balloon fluid 132 within the balloon interior 146 of the balloon 104, such as via the plasma generator 133 that can be located at the guide distal end 122D of the light guide 122A. In particular, the light emitted at the guide distal end 122D of the light guide 122A energizes the plasma generator 133 to form the plasma within the balloon fluid 132 within the balloon interior 146. The plasma formation causes rapid bubble formation and imparts pressure waves upon the treatment site 106. An exemplary plasma-induced bubble 134 is illustrated in FIG. 1.

In various non-exclusive alternative embodiments, the sub-millisecond pulses of light energy from the light source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of light energy can be delivered to the treatment site 106 at a frequency that can be greater than 5000 Hz or less than one Hz, or any other suitable range of frequencies.

It is appreciated that although the light source 124 is typically utilized to provide pulses of light energy, the light source 124 can still be described as providing a single source beam 124A, i.e. a single pulsed source beam.

The light sources 124 suitable for use can include various types of light sources including lasers and lamps. For example, in certain non-exclusive embodiments, the light source 124 can be an infrared laser that emits light energy in the form of pulses of infrared light. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths, and energy levels that can be employed to achieve plasma in the balloon fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the light sources 124 suitable for use in the catheter system 100 can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter system 100 can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In various non-exclusive alternative embodiments, the catheter system 100 can generate pressure waves having maximum pressures in the range of at least approximately two MPa to 50 MPa, at least approximately two MPa to 30 MPa, or at least approximately 15 MPa to 25 MPa.

The pressure waves can be imparted upon the treatment site 106 from a distance within a range from at least approximately 0.1 millimeters (mm) to greater than approximately 25 mm extending radially from the light guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the light guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide the necessary power to each of the light source 124, the system controller 126, the GUI 127, and the handle assembly 128. The power source 125 can have any suitable design for such purposes.

The system controller 126 is electrically coupled to and receives power from the power source 125. Additionally, the system controller 126 is coupled to and is configured to control the operation of each of the light source 124, and the GUI 127. The system controller 126 can include one or more processors or circuits for purposes of controlling the operation of at least the light source 124, and the GUI 127. For example, the system controller 126 can control the light source 124 for generating pulses of light energy as desired and/or at any desired firing rate.

The system controller 126 can further be configured to control the operation of other components of the catheter system 100 such as the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is effectively utilized to impart pressure onto and induce fractures at the treatment site(s) 106. The GUI 127 can provide the user or operator with information that can be used before, during, and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during the use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications, and/or desires of the user or operator.

As shown in FIG. 1, the handle assembly 128 can be positioned at or near the proximal portion 114 of the catheter system 100, and/or near the source manifold 136. In this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position, and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, and the GUI 127. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126.

In one embodiment, the circuitry 156 can include a printed circuit board having one or more integrated circuits, or any other suitable circuitry. In an alternative embodiment, the circuitry 156 can be omitted or can be included within the system controller 126, which in various embodiments can be positioned outside of the handle assembly 128, e.g., within the multiplexer 123. It is understood that the handle assembly 128 can include fewer or additional components than those specifically illustrated and described herein.

Figure 2:
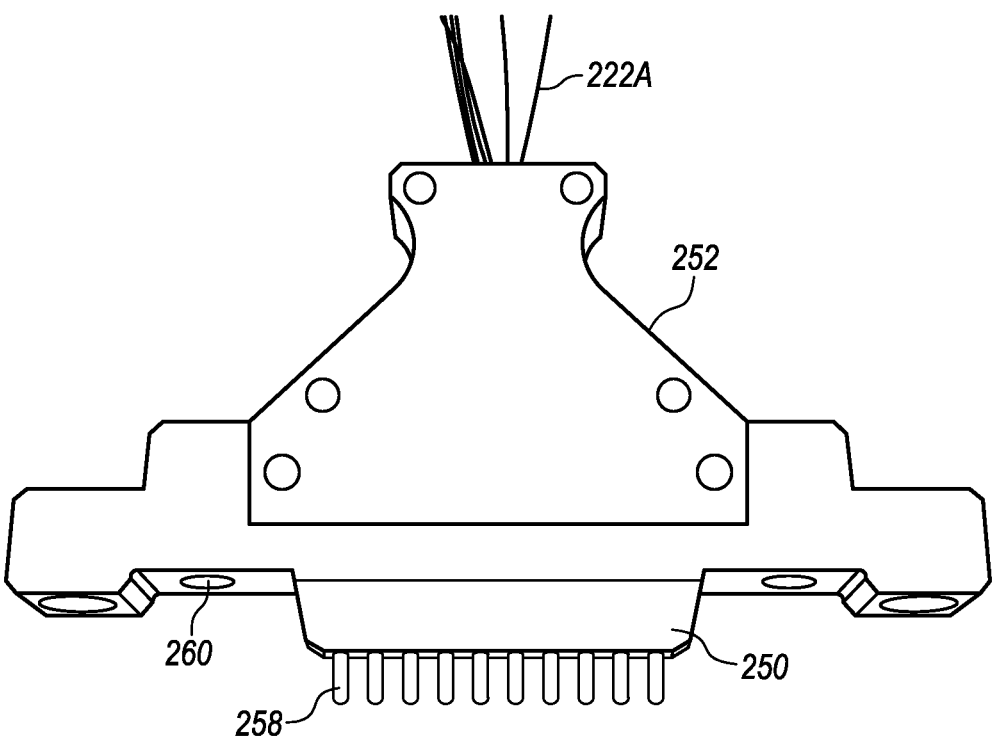
FIG. 2 is a top view of a portion of one embodiment of the catheter system including an embodiment of a guide bundle.

FIG. 2 is a top view of a portion of an embodiment of the catheter system 100 (illustrated in FIG. 1) including an embodiment of a guide bundle 252. As illustrated in the embodiment in FIG. 2, the guide coupling housing 250 houses one or more ferrule assemblies 258 and one or more alignment guide receivers 260. The ferrule assemblies 258 can each include a ferrule 778 (illustrated in FIG. 7, for example), a portion of the individual light guide 222A, including the guide proximal end 122P (illustrated in FIG. 1, for example), and a spring 776 (illustrated in FIG. 7, for example). The ferrule assembly 258 can retain the ferrule 778. In certain embodiments, the light guide 222A can be engaged by a ferrule assembly 258. In particular, the guide proximal end 122P can be terminated into individual ferrules 778 of the ferrule assembly 258. The ferrule assembly 258 can be configured to provide increased localization and improved alignment guides that enable each ferrule 778 to be inserted into receptacle holes 468 (illustrated in FIG. 4, for example) within the receptacle assembly 462 (illustrated in FIG. 4, for example) without damaging the ferrules 778.

The ferrule assembly 258 can vary depending on the design requirements of the catheter system 100, the light guide 222A, the guide proximal end 122P, and/or guide bundle 252. It is understood that the ferrule assembly 258 can include additional systems, subsystems, components, and elements than those specifically shown and/or described herein. Additionally, or alternatively, the ferrule assembly 258 can omit one or more of the systems, subsystems, and elements that are specifically shown and/or described herein. The ferrule assembly 258 can be positioned in any suitable location, including those shown in FIG. 2.

The ferrule assembly 258 can vary in shape. In some embodiments, the ferrule assembly 258 can be substantially plug-shaped, as shown in the embodiment illustrated in FIG. 2. In other embodiments, the ferrule assembly 258 can be substantially cylindrical-shaped, prism-shaped, cube-shaped, cuboid-shaped, and/or tube-shaped.

The ferrule assembly 258 can be formed with any suitable material. In certain embodiments, the ferrule assembly 258 can be at least partially formed from a metal, a plastic, a polymer, a ceramic, a composite, and/or an organic material. In other embodiments, the ferrule assembly 258 can be formed using mold-injected plastics.

Figure 4:
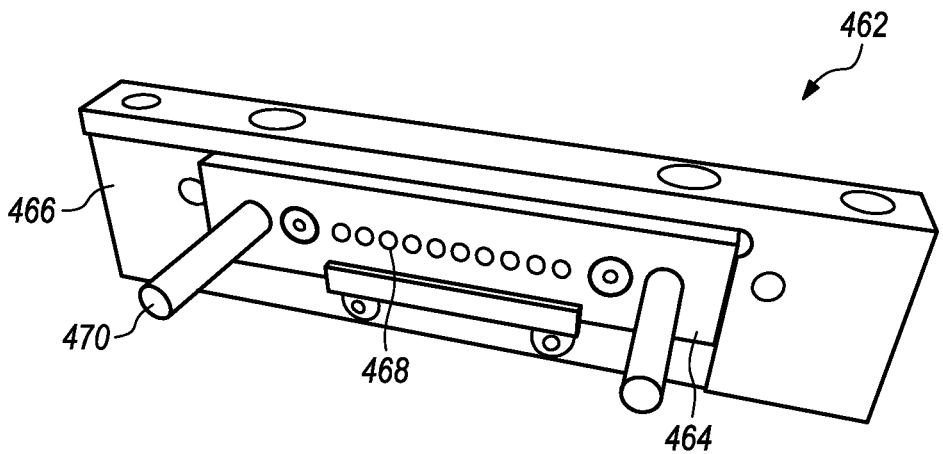
FIG. 4 is a perspective front view of a portion of an embodiment of the catheter system including one embodiment of a receptacle assembly.

The alignment guide receiver 260 receives an alignment guide 470 (illustrated in FIG. 4, for example). The alignment guide receiver 260 can be configured to improve the mating of the ferrule 778 with the receptacle hole 468 within the receptacle assembly 462.

The alignment guide receiver 260 can vary depending on the design requirements of the catheter system 100, the guide bundle 252, and/or the alignment guide 470. It is understood that the alignment guide receiver 260 can include additional systems, subsystems, components, and elements than those specifically shown and/or described herein. Additionally, or alternatively, the alignment guide receiver 260 can omit one or more of the systems, subsystems, and elements that are specifically shown and/or described herein. The alignment guide receiver 260 can be positioned in any suitable location, including those shown in FIG. 2.

In the embodiment shown in FIG. 2, the alignment guide receiver 260 is a pin receiver. Non-limiting, non-exclusive examples of suitable alignment guide receivers include (i) a guide groove of a tongue and groove system, (ii) a guide slot of a tab and slot system, and (iii) a guide channel of a rail and channel system.

Figure 3:
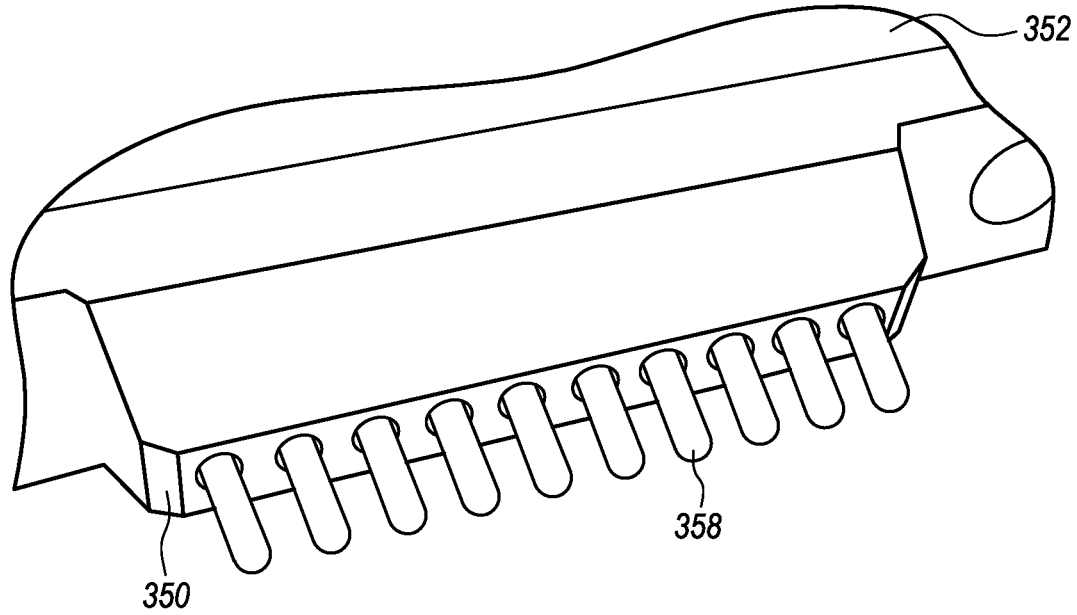
FIG. 3 is a perspective front view of a portion of an embodiment of the catheter system including an embodiment of the guide bundle.

FIG. 3 is a perspective front view of a portion of an embodiment of the catheter system 100 (illustrated in FIG. 1) including an embodiment of a guide bundle 352. In particular, greater detail of the shape and design of the embodiments of the guide coupling housing 350, the guide bundle 352, and the ferrule assembly 358 are illustrated in FIG. 3. For example, as shown in FIG. 3, the guide coupling housing 350 can have a substantially trapezoidal side-profile and a substantially trapezoidal-prism shape. The guide coupling housing 350 can extend outwardly from the guide bundle 352. The guide coupling housing 350 can include one or more apertures, each of the ferrule assemblies 358 can extend through corresponding apertures. As illustrated in the embodiment in FIG. 3, the ferrule assemblies 358 can be substantially cylindrical with a partially spherical end portion. The ferrule assemblies 358 can include an opening or orifice in order to receive the guide beams 122B (illustrated in FIG. 1) from the multiplexer 128 (Illustrated in FIG. 1).

FIG. 4 is a perspective front view of a portion of an embodiment of the catheter system 100 (illustrated in FIG. 1) including an embodiment of a receptacle assembly 462. As illustrated in the embodiment in FIG. 4, the receptacle assembly 462 can include one or more of a receptacle block 464, a receptacle housing 466, a receptacle hole 468, and an alignment guide 470. The receptacle assembly 462 can be configured to mate with the guide bundle 252 (illustrated in FIG. 2, for example) so that the guide beams 122B are aligned with each of the light guides 222A (illustrated in FIG. 2, for example) within the guide bundle 252.

The receptacle assembly 462 can vary depending on the design requirements of the catheter system 100, the light guides 222A, the guide bundle 252 and/or the ferrule assembly 358 (illustrated in FIG. 3, for example). It is understood that the receptacle assembly 462 can include additional systems, subsystems, components, and elements than those specifically shown and/or described herein. Additionally, or alternatively, the receptacle assembly 462 can omit one or more of the systems, subsystems, and elements that are specifically shown and/or described herein. The receptacle assembly 462 can be positioned in any suitable location, including those shown in FIG. 4.

The receptacle assembly 462 can be formed from any suitable material. In some embodiments, the components of the receptacle assembly 462 can be formed at least partially from a metal, a plastic, a ceramic, a polymer, a composite, and/or an organic material. In certain embodiments, the components of the receptacle assembly 462 can be formed from a hardened stainless steel configured to have increased resilience and resistance to wear and tear.

The receptacle block 464 can be configured to receive the guide bundle 252. The receptacle block 464 can vary depending on the design requirements of the catheter system 100, the light guides 222A, the guide bundle 252, and/or the receptacle assembly 462. It is understood that the receptacle block 464 can include additional systems, subsystems, components, and elements than those specifically shown and/or described herein. Additionally, or alternatively, the receptacle block 464 can omit one or more of the systems, subsystems, and elements that are specifically shown and/or described herein. The receptacle block 464 can be positioned in any suitable location, including those shown in FIG. 4.

The receptacle housing 466 can house the receptacle block 464. In some embodiments, the receptacle housing 466 can be coupled to the receptacle block 464. The receptacle housing 466 can vary depending on the design requirements of the catheter system 100, the light guides 222A, the guide bundle 252, the receptacle assembly 462, and/or the receptacle block 464. It is understood that the receptacle housing 466 can include additional systems, subsystems, components, and elements than those specifically shown and/or described herein. Additionally, or alternatively, the receptacle housing 466 can omit one or more of the systems, subsystems, and elements that are specifically shown and/or described herein. The receptacle housing 466 can be positioned in any suitable location, including those shown in FIG. 4.

The receptacle hole 468 can be precision-bored into the receptacle block 464. Alternatively, the receptacle hole 468 can be formed in the receptacle block 464 by any suitable method known in the art. As shown in the embodiment in FIG. 4, one or more receptacle holes 468 can be aligned in a linear array in the receptacle block 464. The receptacle hole 468 can vary depending on the design requirements of the catheter system 100, the light guides 222A, the guide bundle 252, the receptacle assembly 462, and/or the receptacle block 464. It is understood that the receptacle hole 468 can include additional systems, subsystems, components, and elements than those specifically shown and/or described herein. Additionally, or alternatively, the receptacle hole 468 can omit one or more of the systems, subsystems, and elements that are specifically shown and/or described herein.

The receptacle hole 468 can be positioned in any suitable location, including those shown in FIG. 4. The receptacle assembly 462 can include any suitable number of receptacle holes 468 such as 1, 2, 3, 4, 5, 7, 8, 9, or 10 receptacle holes 468. In other embodiments, the receptacle assembly 462 can include greater than 10 receptacle holes 468.

Figure 6:
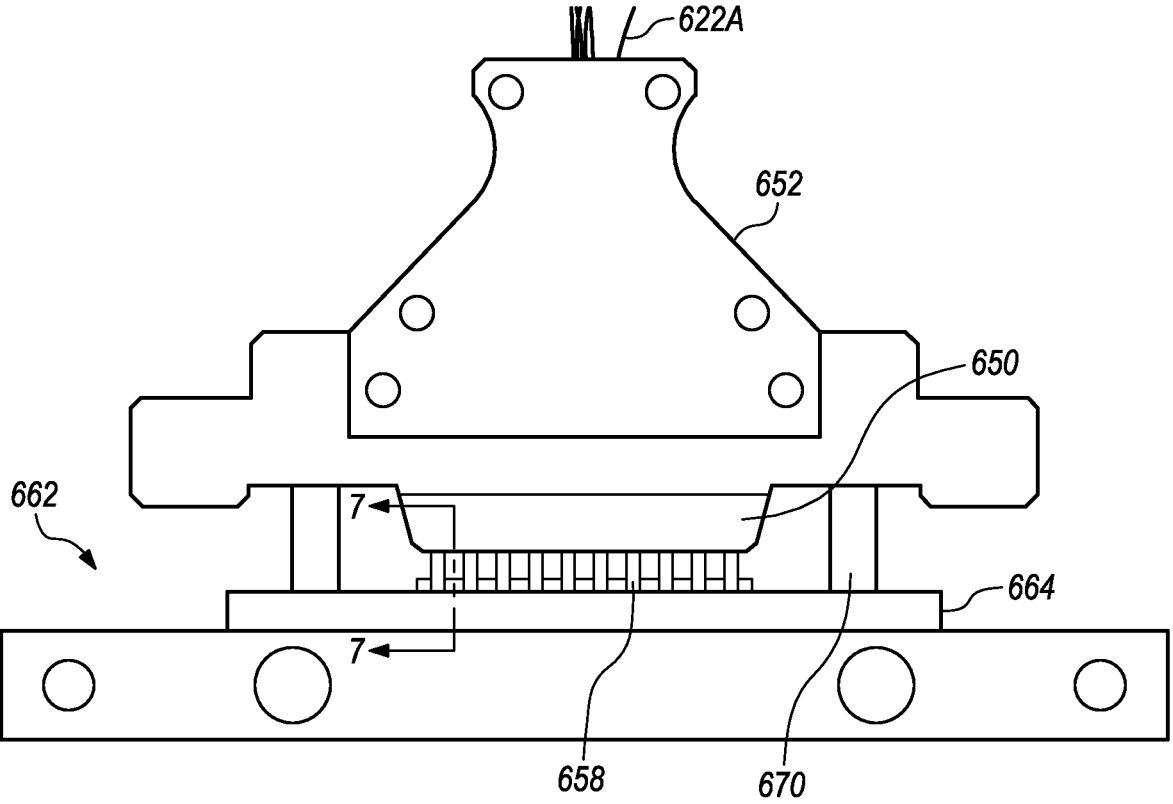
FIG. 6 is a top view of a portion of an embodiment of the catheter system including an embodiment of the guide bundle and the receptacle assembly, the guide bundle being shown in a partially connected state with respect to the receptacle assembly.

The alignment guide 470 can be coupled to the receptacle block 464. The alignment guide 470 can mate with the alignment guide receiver 260 (illustrated in FIG. 2) so that the guide bundle 252 and the receptacle assembly 464 are at least partially aligned and/or coupled (for example, as illustrated in FIG. 6). The alignment guide 470 can vary depending on the design requirements of the catheter system 100, the light guides 222A, the guide bundle 252, the alignment guide receiver 260, the receptacle assembly 462, and/or the receptacle block 464. It is understood that the alignment guide 470 can include additional systems, subsystems, components, and elements than those specifically shown and/or described herein. Additionally, or alternatively, the alignment guide 470 can omit one or more of the systems, subsystems, and elements that are specifically shown and/or described herein.

The alignment guide 470 can be positioned in any suitable location, including those shown in FIG. 4. The alignment guide 470 can be substantially dowel-shaped. The receptacle assembly 462 can include any suitable number of alignment guides 470 such as 1, 2, 3, 4, 5, 7, 8, 9, or 10 alignment guides 470. In other embodiments, the receptacle assembly 462 can include greater than 10 alignment guides 470. The alignment guide 470 can be any suitable alignment guide 470 known within the art. In the embodiment shown in FIG. 4, the alignment guide 470 is a guide pin. Non-limiting, non-exclusive examples of suitable alignment guides include (i) a guide tongue of a tongue and groove system, (ii) a guide tab of a tab and slot system, and (iii) a guide rail of a rail and channel system.

Figure 5:
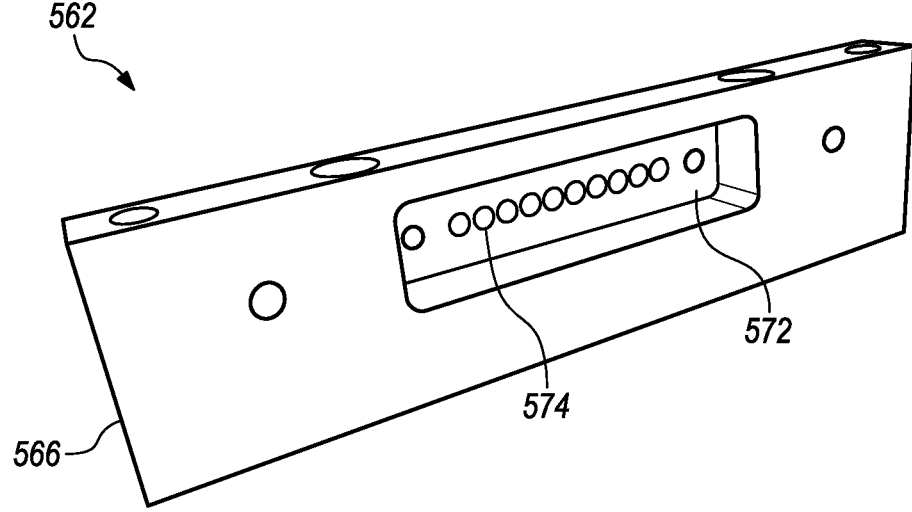
FIG. 5 is a perspective rear view of a portion of an embodiment of the catheter system including one embodiment of the receptacle assembly.

FIG. 5 is a perspective rear view of a portion of an embodiment of the catheter system 100 (illustrated in FIG. 1) including an embodiment of a receptacle assembly 562. As illustrated in the embodiment displayed in FIG. 5, the receptacle assembly 562 can include a receptacle housing 566 and a backing plate 572 including one or more alignment holes 574.

The backing plate 572 can be configured to receive a proximal end face of the ferrules 766. The backing plate 572 can provide a precision reference plane for aligning the guide beams 1226 from the multiplexer 128 to each of the corresponding light guides 122A (illustrated in FIG. 1). The alignment holes 574 can be precision-bored into the backing plate 572. The alignment holes 574 can be formed into the backing plate 572 using any suitable method known in the art. The alignment holes 574 can be configured to couple the focused guide beams 122B with each of the corresponding light guides 122A.

The backing plate 572 and alignment holes 574 can vary depending on the design requirements of the catheter system 100, the light guides 222A, the guide bundle 252, the alignment guide receiver 260, the receptacle assembly 462, and/or the receptacle block 464. It is understood that the backing plate 572 can include additional systems, subsystems, components, and elements than those specifically shown and/or described herein. Additionally, or alternatively, the backing plate 572 can omit one or more of the systems, subsystems, and elements that are specifically shown and/or described herein. The backing plate 572 and alignment holes 574 can be positioned in any suitable location, including those shown in FIG. 5. In certain embodiments, the alignment holes 574 can have a smaller diameter than the diameter of the ferrule 778. The alignment holes 574 can have a sufficiently-sized diameter in order to accommodate the entire guide beam 128B without clipping.

FIG. 6 is a top view of a portion of an embodiment of the catheter system 100 (illustrated in FIG. 1) including an embodiment of a guide bundle 652 including light guides 622A and a receptacle assembly 662, the guide bundle 652 being shown in a partially connected state with respect to the receptacle assembly 662. In particular, in the embodiment illustrated in FIG. 6, the guide coupling housing 650 is advanced so that the ferrule assemblies 658 and the alignment guides 670 are partially seated within the receptacle block 664.

Figure 7:
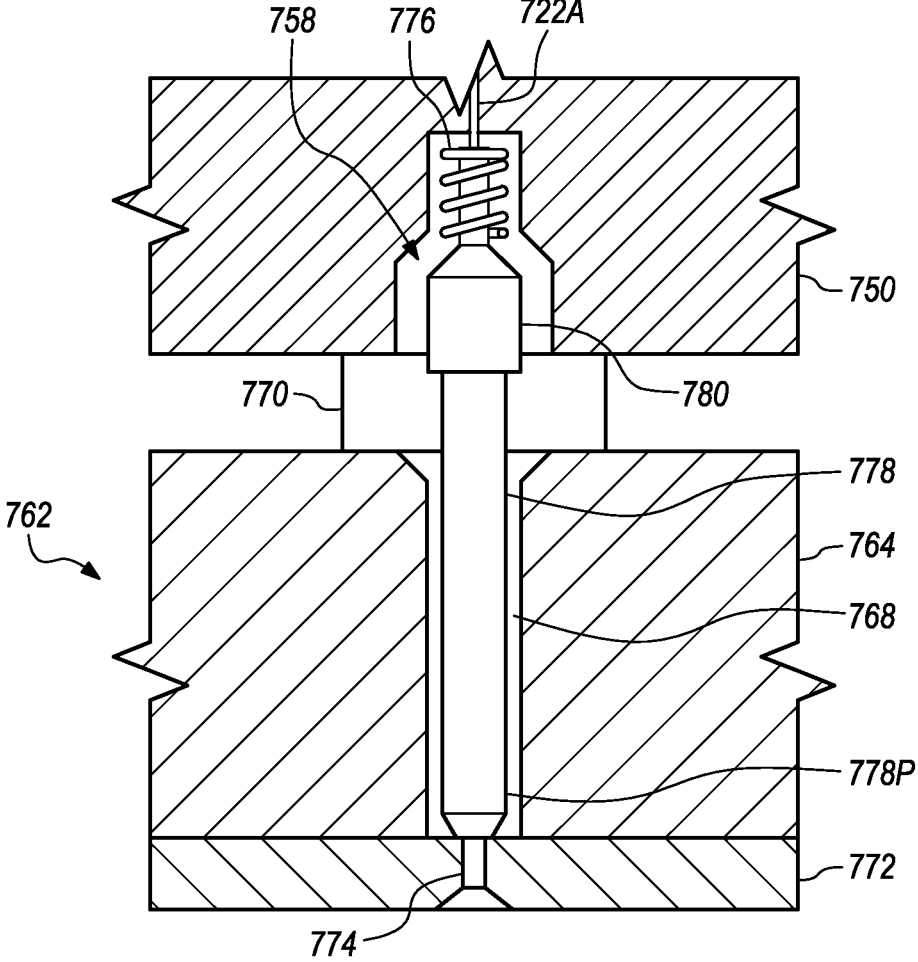
FIG. 7 is a simplified cross-sectional view of a portion of an embodiment of the catheter system taken on line 7-7 in FIG. 6, the catheter system including one embodiment of a guide coupling housing and the receptacle assembly, the guide coupling housing being shown in a partially connected state with respect to the receptacle assembly.

FIG. 7 is a simplified cross-sectional view of a portion of an embodiment of the catheter system 100 (illustrated in FIG. 1) taken on line 7-7 in FIG. 6, the catheter system 100 including an embodiment of a guide coupling housing 750 including light guides 722A and a receptacle assembly 762, the guide coupling housing 750 being shown in a partially connected state with respect to the receptacle assembly 762. In particular, in the embodiment illustrated in FIG. 7, the guide coupling housing 750 is advanced so that the ferrule assemblies 758 and the alignment guides 770 are partially seated within the receptacle block 764. In FIG. 7, the ferrule assembly 758 is (i) partially extended through the receptacle hole 768, and (ii) partially engaged with the backing plate 772 of the receptacle assembly 762 so that the alignment hole 774 is aligned with the ferrule assembly 758. As illustrated in the embodiment displayed in FIG. 7, the ferrule assembly 758 can further include a spring 776, a ferrule 778, and a ferrule collar 780.

The spring 776 can engage the ferrule 778 and/or the ferrule collar 780 within the ferrule assembly 758. The spring 776 can be configured to provide an insertion force when the ferrule assembly 758 is inserted into the receptacle hole 768. The spring 776 can vary depending on the design requirements of the catheter system 100, the light guides 222A, the guide coupling housing 750, the receptacle assembly 762, the receptacle hole 768, the ferrule 778, and/or the ferrule collar 780. It is understood that the spring 776 can include additional systems, subsystems, components, and/or elements than those specifically shown and/or described herein. Additionally, or alternatively, the spring 776 can omit one or more of the systems, subsystems, and elements that are specifically shown and/or described herein. The spring 776 can be positioned in any suitable location, including those shown in FIG. 7. The spring 776 can be a spiral spring.

The ferrule 778 can engage the guide proximal end 122P (illustrated in FIG. 1) of the light guide 722A within the ferrule assembly 758. The ferrule 778 can fasten, reinforce, and/or seal the guide proximal end 122P of the light guide 722A. The ferrule 778 can vary depending on the design requirements of the catheter system 100, the light guides 722A, the guide coupling housing 750, the receptacle assembly 762, the receptacle hole 768, the spring 776, and/or the ferrule collar 780. It is understood that the ferrule 778 can include additional systems, subsystems, components, and elements than those specifically shown and/or described herein. Additionally, or alternatively, the ferrule 778 can omit one or more of the systems, subsystems, and elements that are specifically shown and/or described herein. The ferrule 778 can be positioned in any suitable location, including those shown in FIG. 7.

The ferrule 778 can be formed from any suitable material. In certain embodiments, the ferrule 778 can be partially formed from a metal, a plastic, a ceramic, a polymer, a composite, and/or an organic material. The ferrule 778 can have a proximal end face 778P. In some embodiments, the proximal end face 778P can engage the backing plate 772 when the ferrule 778 is at least partially inserted in the receptacle hole 768. As shown in FIG. 7, the alignment hole 774 can have a smaller diameter than the ferrule 778 so that the proximal end face 778P of the ferrule 778 is seated on the alignment hole 774.

The ferrule collar 780 can back the ferrule 778. The ferrule collar 780 can be seated within the spring 776. The ferrule 778 can vary depending on the design requirements of the catheter system 100, the light guides 222A, the guide coupling housing 750, the receptacle assembly 762, the receptacle hole 768, the spring 776, and/or the ferrule collar 780. It is understood that the ferrule 778 can include additional systems, subsystems, components, and elements than those specifically shown and/or described herein. Additionally, or alternatively, the ferrule 778 can omit one or more of the systems, subsystems, and elements that are specifically shown and/or described herein. The ferrule 778 can be positioned in any suitable location, including those shown in FIG. 7.

Figure 8:
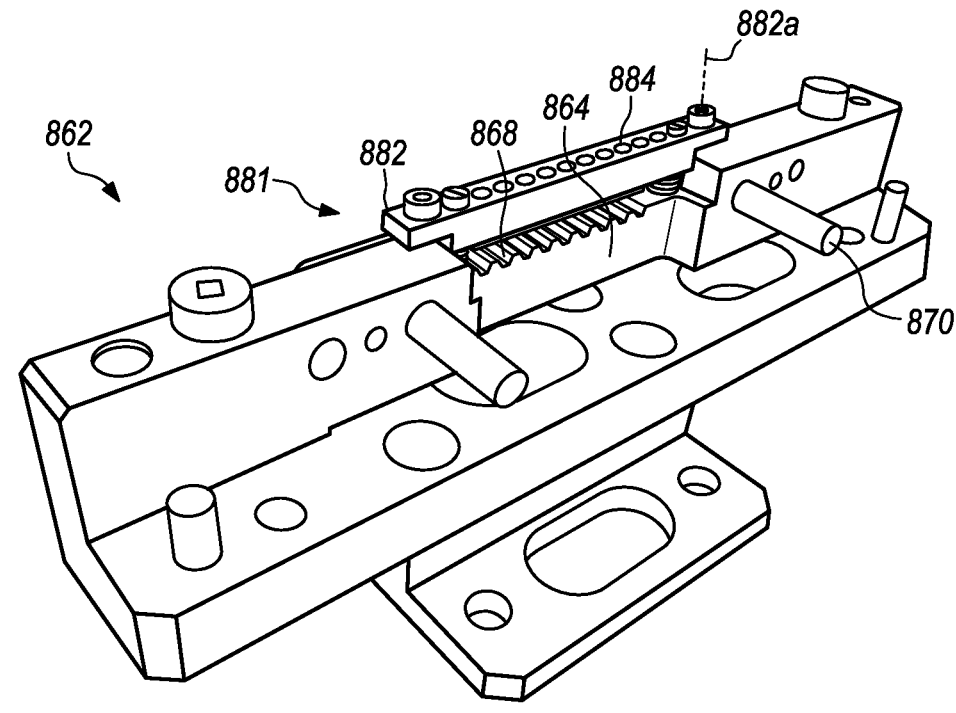
FIG. 8 is a perspective front view of a portion of an embodiment of the catheter system including one embodiment of the receptacle assembly.

FIG. 8 is a perspective front view of a portion of an embodiment of the catheter system 100 (illustrated in FIG. 1) including an embodiment of a receptacle assembly 862. FIG. 8 illustrates one embodiment of the receptacle assembly 862 that is slightly different than the other embodiments described herein. In the embodiment illustrated in FIG. 8, the receptacle block 864 includes one or more receptacle holes 868 that are formed in a linear array as v-grooves, rather than singular holes.

In some embodiments, the v-groove receptacle holes 868 shown in FIG. 8 can be formed by cutting into a hardened block of stainless steel. The v-grooves can be electrical discharge machine cut into the receptacle holes 868. The v-grooves provide at least two contact lines while the ferrule 778 is retained within the receptacle hole 868. In the embodiment illustrated in FIG. 8, the receptacle assembly 862 can include a retainer assembly 881 including a clamping bar 882 having a clamping bar axis 882a, and a plunger 884. The retaining assembly 881 retains the ferrule 778 within the receptacle hole 868. The retaining assembly 881 can be configured to reduce and/or inhibit the insertion forces required to retain the ferrule 778 within the receptacle hole 868.

The retaining assembly 881 can vary depending on the design requirements of the catheter system 100, the receptacle assembly 862, and/or the ferrule 778. It is understood that the retaining assembly 881 can include additional systems, subsystems, components, and elements than those specifically shown and/or described herein. Additionally, or alternatively, the retaining assembly 881 can omit one or more of the systems, subsystems, and elements that are specifically shown and/or described herein. The retaining assembly 881 can be positioned in any suitable location, including those shown in FIG. 8.

The clamping bar 882 clamps the ferrule 778 into the receptacle hole 868. The clamping bar 882 can be moved about the clamping bar axis 882a to apply and/or remove a retaining force onto one or more ferrule 778 (for example, see FIG. 10). In certain embodiments, the clamping bar 882 can be raised and lowered thereby allowing (i) movement of the ferrule 778 upon insertion, and (ii) retention of the ferrule 778 once the proximal end face 778P is seated against the backing plate 772 (illustrated in FIG. 7) and the clamping bar 882 is lowered to retain the ferrule 778.

The clamping bar 882 can vary depending on the design requirements of the catheter system 100, the receptacle assembly 862, the ferrule 778, the retaining assembly 881, and/or the plunger 884. It is understood that the clamping bar 882 can include additional systems, subsystems, components, and elements than those specifically shown and/or described herein. Additionally, or alternatively, the clamping bar 882 can omit one or more of the systems, subsystems, and elements that are specifically shown and/or described herein. The clamping bar 882 can be positioned in any suitable location, including those shown in FIG. 8.

The clamping bar 882 can include a compliant material and/or wave springs that are configured to spread a retaining force across the ferules 778 so that each of the ferrules 778 is retained within a corresponding receptacle hole 868. The clamping bar 882 can retain the ferrule 778 so that the ferrule 778 is not free-floating within the receptacle hole 868. The clamping bar 882 can also be configured to provide a uniform or substantially uniform retaining force to the ferrules 778, as known in the art.

The plunger 884 engages (e.g., plunges) the ferrule 778 into the receptacle hole 868 so that the ferrule 778 is retained in place. In some embodiments, the plunger 884 engages the upper edges of the ferrule 778, seating it into the v-groove of the receptacle hole 868. The plunger 884 can vary depending on the design requirements of the catheter system 100, the receptacle assembly 862, the ferrule 778, the retaining assembly 881, and/or the clamping bar 882. It is understood that the plunger 884 can include additional systems, subsystems, components, and elements than those specifically shown and/or described herein. Additionally, or alternatively, the plunger 884 can omit one or more of the systems, subsystems, and elements that are specifically shown and/or described herein.

The plunger 884 can be positioned in any suitable location, including those shown in FIG. 8. The plunger 884 can be substantially similar in form and/or function as a ball-spring plunger. The plunger 884 can be integrated into the clamping bar 882 (for example, as illustrated in FIG. 8).

Figure 9:
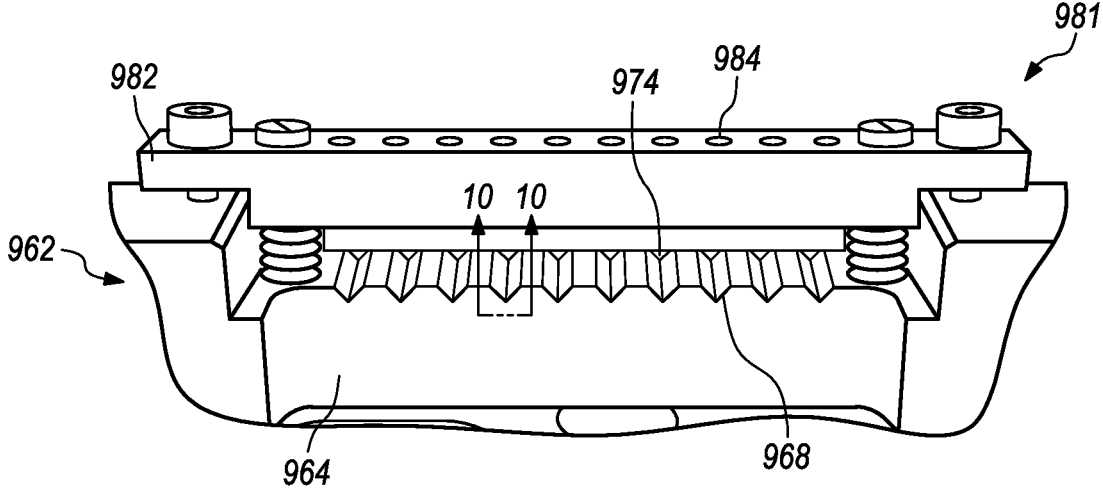
FIG. 9 is a front elevation view of a portion of an embodiment of the catheter system including one embodiment of a portion of the receptacle assembly.

FIG. 9 is a front elevation view of a portion of an embodiment of the catheter system 100 (illustrated in FIG. 1) including an embodiment of a portion of a receptacle assembly 962. FIG. 9 illustrates one embodiment of the receptacle assembly 962 that is slightly different than the other embodiments described herein. In the embodiment illustrated in FIG. 9, greater detail is shown of the interior of the receptacle block 964 including a receptacle hole 968. In FIG. 9, the alignment hole 974 and the retaining assembly 981 including the clamping bar 982 and the plunger 984 are shown.

Figure 10:
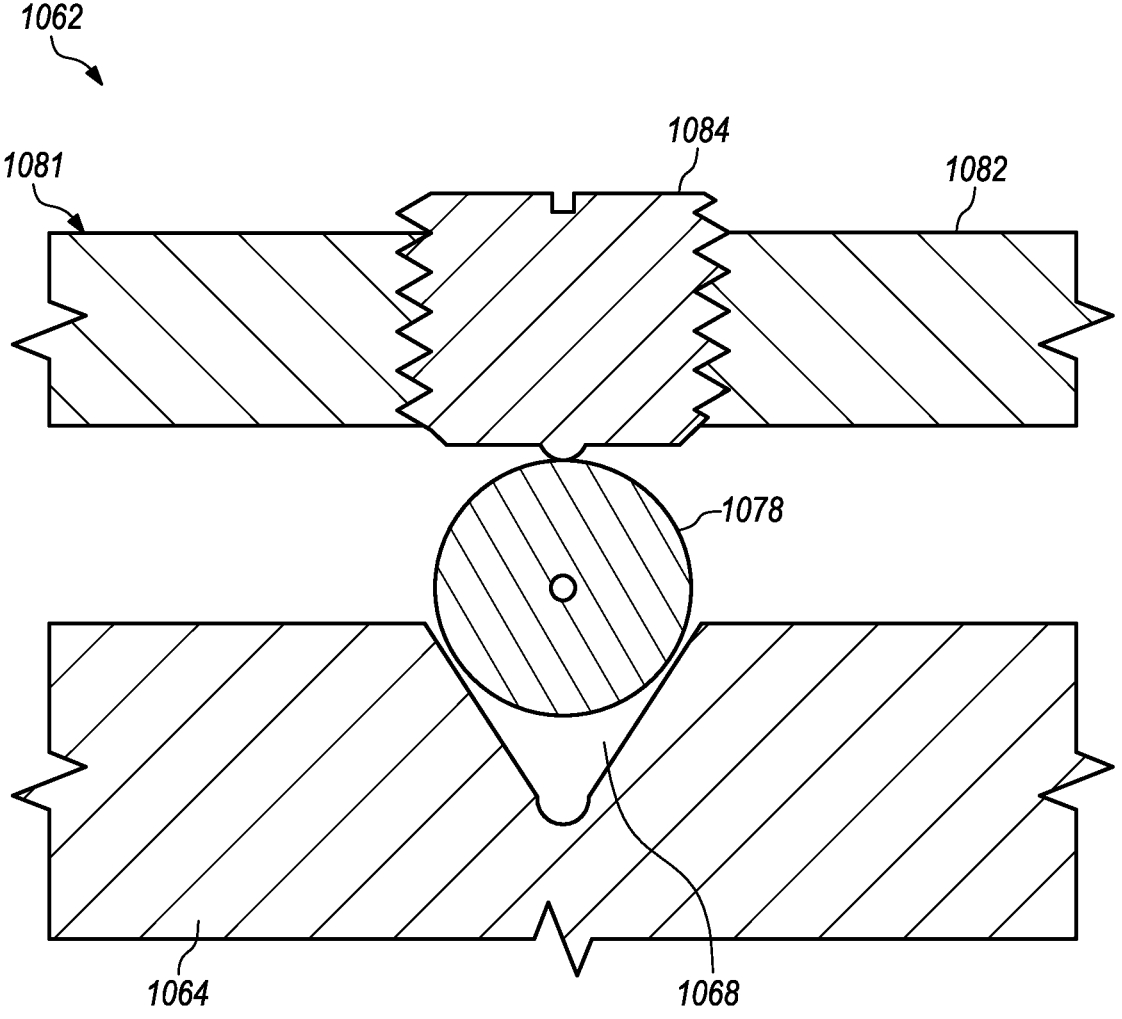
FIG. 10 is a simplified cross-sectional view of a portion of an embodiment of the catheter system taken on line 10-10 in FIG. 9, the catheter system including one embodiment of the receptacle assembly.

FIG. 10 is a simplified cross-sectional view of a portion of an embodiment of the catheter system 100 (illustrated in FIG. 1) taken on line 10-10 in FIG. 9, the catheter system 100 including an embodiment of a receptacle assembly 1062. FIG. 10 illustrates one embodiment of the receptacle assembly 1062 that is slightly different than the other embodiments described herein. In the embodiment illustrated in FIG. 10, the receptacle block 1064 includes one or more receptacle holes 1068 that are formed in a linear array as v-grooves, rather than singular holes. In the embodiment illustrated in FIG. 10, the receptacle assembly 1062 can include a retainer assembly 1081 including a clamping bar 1082, and a plunger 1084. The retaining assembly 1081 retains the ferrule 1078 within the receptacle hole 1068. The retaining assembly 1081 can be configured to reduce and/or inhibit the insertion forces required to retain the ferrule 1078 within the receptacle hole 1068. The clamping bar 1082 clamps the ferrule 1078 into the receptacle hole 1068.

This technology provides a connector solution for multiple optical channels that improves optical coupling to an individual light guide organized in a multi-channel array. The technology can utilize individual, low-cost ferrules to terminate the light guides. These ferrules are carried in ferrule assembly included within the guide bundle. In some embodiments, the guide bundle aligns the ferrules into a linear array. The ferrules can float within the ferrule assembly with low location tolerances. The connectorized ferrule assembly can mate with a high-precision receptacle assembly including a receptacle plate and/or receptacle block. Mechanical features in the receptacle assembly capture and align the individual ferrules. These features can align the floating ferrules in an improved precision array with tightly controlled tolerances. This technology allows a single, stable energy source to be channeled sequentially through a plurality of channels with a variable number.

Specific advantages this technology provides include: 1) enabling the use of low cost, high-precision, singular ferrules on a single-use device for an increased-reliability connection thereby reducing production costs, 2) reducing the system performance dependence on the assembly of light guides into a ferrule block and the associated mechanical tolerances related to their location in a multi-channel array, 3) reducing the performance dependence on accuracy of connecting and aligning the multi-channel array to the multiplexer, 4) reducing the need for a high-cost, high-precision monolithic ferrule block.

In some embodiments the light guides are optical fibers, the energy source is a pulsed laser and the emitters are plasma generators. In its simplest form, the multiplexer is a precision linear mechanism that translates coupling optics along a linear path. This approach requires a single degree of freedom. A connector block organizes the individual optical fibers into a liner pattern with precise interval spacing.

In certain embodiments, the linear translation mechanism is electronically controlled by the system to line the beam path up sequentially with each individual fiber organized in the ferrule. The translating mechanism carries necessary beam directing optics and focusing optics to focus the laser energy onto each fiber for optimal coupling. That way, the low divergence of the laser beam over the short distance of motion of the translated coupling mechanism has a minimum impact on coupling efficiency to the fiber. The system drives the mechanism to align the beam path with a selected fiber optic channel and then fires the laser in pulsed or semi-continuous wave mode.

This system and method can be implemented for any multiplexer configuration either linear, circular, patterned, or scanned. In some embodiments, the system can include a probe and a plurality of primary laser beams that can be combined and spot traced by beam paths that are correlated to the parametric motion of the multiplexer mechanism.

It is appreciated that the systems and methods of optical alignment provided herein address multiple potential issues with the performance, reliability, and proper usage of an IVL catheter, in particular one that utilizes an energy source to create a localized plasma which in turn produces a high energy bubble inside a balloon. Specific problems solved by the systems and methods disclosed herein include:

1) The technology disclosed herein reduces the optical coupling dependence on the precision and mechanical tolerance stack-ups of assemblies and true alignment for light guides (such as optical fibers), ferrules, connectors, and receptacles, enabling the use of low-cost, low-precision components on the single-use device and improve the cost of goods sold.

2) The technology disclosed herein reduces the multiplexer performance dependence on the accuracy of positioning mechanism in the multiplexer and associated quality and precision of its optical and mechanical components thereby improving speed and performance of the multiplexer and multi-channel ferrule system.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A catheter system for treating a treatment site within or adjacent to a vessel wall or a heart valve, the catheter system comprising:
a first light guide that receives a light energy from a light source, the first light guide having a guide proximal end;
a second light guide that receives the light energy from the light source, the second light guide having a guide proximal end;
a guide bundle that is in optical communication with the light source, the guide bundle bundling the first light guide and the second light guide, the guide bundle including a first ferrule that engages the guide proximal end of the first light guide and a second ferrule that engages the guide proximal end of the second light guide; and
a receptacle assembly including (i) a first receptacle hole that is configured to receive the first ferrule, and (ii) a second receptacle hole that is configured to receive the second ferrule;
wherein the receptacle assembly includes a retainer assembly including a clamping bar in direct contact with the first ferrule and the second ferrule such that the clamping bar applies a retaining force directly onto the first ferrule and the second ferrule so as to retain (i) the first ferrule in the first receptacle hole, and
(ii) the second ferrule in the second receptacle hole.

2. The catheter system of claim 1 wherein the retainer assembly further includes a plunger that is configured to contact (i) at least a portion of the first ferrule so that the first ferrule is retained in the first receptacle hole, and (ii) at least a portion of the second ferrule so that the second ferrule is retained in the second receptacle hole.

3. The catheter system of claim 2 wherein the plunger is a ball spring plunger.

4. The catheter system of claim 2 wherein the plunger is integrated into the clamping bar.

5. The catheter system of claim 1 wherein the receptacle assembly further includes a receptacle block and a backing plate that is coupled to the receptacle block, the backing plate being configured to engage the first ferrule and the second ferrule.

6. The catheter system of claim 5 wherein the first receptacle hole and the second receptacle hole are formed as v-grooves in the receptacle block.

7. The catheter system of claim 5 wherein the first receptacle hole and the second receptacle hole are each formed in the receptacle block, the first receptacle hole and the second receptacle hole being aligned on a same linear axis as one another.

8. The catheter system of claim 5 wherein the backing plate includes (i) a first alignment hole that is configured to align a first guide beam with the first light guide, and (ii) a second alignment hole that is configured to align a second guide beam with the second light guide.

9. The catheter system of claim 1 further comprising an alignment guide and an alignment guide receiver that are configured to engage one another to guide alignment between the first ferrule and the first receptacle hole and between the second ferrule and the second receptacle hole; wherein the alignment guide is coupled to one of the guide bundle and the receptacle assembly; and wherein the alignment guide receiver is coupled to the other of the guide bundle and the receptacle assembly.

10. The catheter system of claim 1 wherein the guide bundle further includes (i) a first ferrule assembly including the first ferrule and a first spring that engages the first ferrule, the first spring being configured to provide an insertion force when the first ferrule is inserted into the first receptacle hole, and (ii) a second ferrule assembly including the second ferrule and a second spring that engages the second ferrule, the second spring being configured to provide an insertion force when the second ferrule is inserted into the second receptacle hole.

11. The catheter system of claim 1 wherein the light source includes a laser, and wherein each of the first light guide and the second light guide includes an optical fiber.

12. A catheter system for treating a treatment site within or adjacent to a vessel wall or a heart valve, the catheter system comprising:

a light source that generates light energy;

a first light guide that receives the light energy from the light source, the first light guide having a guide proximal end;

a second light guide that receives the light energy from the light source, the second light guide having a guide proximal end;

a guide bundle that is in optical communication with the light source, the guide bundle bundling the first light guide and the second light guide, the guide bundle including a first ferrule that engages the guide proximal end of the first light guide and a second ferrule that engages the guide proximal end of the second light guide; and a receptacle assembly including (i) a receptacle block, (ii) a first receptacle hole that is configured to receive the first ferrule, and (iii) a second receptacle hole that is configured to receive the second ferrule;

wherein the first receptacle hole and the second receptacle hole are formed as v-grooves in the receptacle block;

wherein the receptacle assembly further includes a retainer assembly including (i) a clamping bar in direct contact with the first ferrule and the second ferrule such that the clamping bar applies a retaining force directly onto the first ferrule and the second ferrule, and (ii) a plunger that is configured to contact at least a portion of the first ferrule so that the first ferrule is retained in the first receptacle hole, and at least a portion of the second ferrule so that the second ferrule is retained in the second receptacle hole, the plunger being integrated into the clamping bar.

13. The catheter system of claim 12 wherein the receptacle assembly further includes a backing plate that is coupled to the receptacle block, the backing plate being configured to engage the first ferrule and the second ferrule.

14. The catheter system of claim 13 wherein the backing plate includes (i) a first alignment hole that is configured to align a first guide beam with the first light guide, and (ii) a second alignment hole that is configured to align a second guide beam with the second light guide.

15. The catheter system of claim 12 wherein the first receptacle hole and the second receptacle hole are aligned on a same linear axis as one another.

16. The catheter system of claim 12 further comprising an alignment guide and an alignment guide receiver that are configured to engage one another to guide alignment between the first ferrule and the first receptacle hole and between the second ferrule and the second receptacle hole; wherein the alignment guide is coupled to one of the guide bundle and the receptacle assembly; and wherein the alignment guide receiver is coupled to the other of the guide bundle and the receptacle assembly.

17. The catheter system of claim 12 wherein the guide bundle further includes (i) a first ferrule assembly including the first ferrule and a first spring that engages the first ferrule, the first spring being configured to provide an insertion force when the first ferrule is inserted into the first receptacle hole, and (ii) a second ferrule assembly including the second ferrule and a second spring that engages the second ferrule, the second spring being configured to provide an insertion force when the second ferrule is inserted into the second receptacle hole.

18. The catheter system of claim 12 wherein the light source includes a laser, and wherein each of the first light guide and the second light guide includes an optical fiber.

19. The catheter system of claim 12 wherein the clamping bar is configured to spread a retaining force across the ferrules so that each ferrule is retained within a corresponding receptacle hole.

20. A catheter system for treating a treatment site within or adjacent to a vessel wall or a heart valve, the catheter system comprising:

a light source that generates light energy;

a first light guide that receives the light energy from the light source, the first light guide having a guide proximal end;

a second light guide that receives the light energy from the light source, the second light guide having a guide proximal end;

a guide bundle that is in optical communication with the light source, the guide bundle bundling the first light guide and the second light guide, the guide bundle including a first ferrule that engages the guide proximal end of the first light guide and a second ferrule that engages the guide proximal end of the second light guide; and a receptacle assembly including (i) a first receptacle hole that is configured to receive the first ferrule, and (ii) a second receptacle hole that is configured to receive the second ferrule;

wherein the receptacle assembly includes a retainer assembly including a clamping bar that is configured to apply a retaining force onto the first ferrule and the second ferrule so as to retain (i) the first ferrule in the first receptacle hole, and (ii) the second ferrule in the second receptacle hole;

wherein the clamping bar is configured to be adjustable about a clamping bar axis, the clamping bar including a compliant material in direct contact with the ferrules and spreads a retaining force across the ferrules so that each ferrule is retained within a corresponding receptacle hole when the ferrules are received in the receptacle assembly.

* * * * *